(12) United States Patent
Dahl

(10) Patent No.: US 11,730,729 B2
(45) Date of Patent: Aug. 22, 2023

(54) QUINOLINES THAT MODULATE SERCA AND THEIR USE FOR TREATING DISEASE

(71) Applicant: Neurodon Corporation, Crown Point, IN (US)

(72) Inventor: Russell Dahl, Saint John, IN (US)

(73) Assignee: Neurodon Corporation, Crown Point, IN (US)

( * ) Notice: Subject to any disclaimer, the term of this patent is extended or adjusted under 35 U.S.C. 154(b) by 0 days.

(21) Appl. No.: 17/401,371

(22) Filed: Aug. 13, 2021

(65) Prior Publication Data

US 2022/0016108 A1   Jan. 20, 2022

Related U.S. Application Data

(63) Continuation-in-part of application No. 16/932,832, filed on Jul. 20, 2020, now abandoned.

(51) Int. Cl.
| | | |
|---|---|---|
| *A61K 31/4706* | (2006.01) | |
| *A61P 3/10* | (2006.01) | |
| *A61K 31/4709* | (2006.01) | |

(52) U.S. Cl.
CPC ...... *A61K 31/4706* (2013.01); *A61K 31/4709* (2013.01); *A61P 3/10* (2018.01)

(58) Field of Classification Search
None
See application file for complete search history.

(56) References Cited

U.S. PATENT DOCUMENTS

| | | |
|---|---|---|
| 4,530,931 A | 7/1985 | Musser et al. |
| 5,968,959 A | 10/1999 | Haikala et al. |
| 5,994,362 A | 11/1999 | Gormley et al. |
| 6,008,230 A | 12/1999 | Oku et al. |
| 6,265,421 B1 | 7/2001 | Pystynen et al. |
| 8,431,356 B2 | 4/2013 | Thomas et al. |
| 8,642,660 B2 | 2/2014 | Goldfarb |
| 8,680,139 B2 | 3/2014 | Cao et al. |
| 8,685,970 B2 | 4/2014 | Vu et al. |
| 10,383,868 B2 | 8/2019 | Dahl |
| 10,772,881 B2 | 9/2020 | Dahl |
| 2006/0183909 A1 | 8/2006 | Schmitt et al. |
| 2007/0254894 A1 | 11/2007 | Kane et al. |
| 2008/0021063 A1 | 1/2008 | Kazantsev |
| 2008/0293699 A1 | 11/2008 | Reed et al. |
| 2010/0184739 A1 | 7/2010 | Sheth et al. |
| 2010/0222346 A1 | 9/2010 | Amberg et al. |
| 2011/0046110 A1 | 2/2011 | Vu et al. |
| 2013/0210844 A1 | 8/2013 | Gharat et al. |
| 2017/0281611 A1 | 10/2017 | Dahl |
| 2019/0151303 A1 | 5/2019 | Dahl |
| 2020/0347038 A1 | 11/2020 | Dahl |
| 2022/0048898 A1 | 5/2022 | Dahl |

FOREIGN PATENT DOCUMENTS

| | | |
|---|---|---|
| CA | 1261835 A | 9/1989 |
| CN | 106966973 A | 7/2017 |
| EA | 021938 B1 | 10/2015 |
| EP | 0173516 A2 | 3/1986 |
| EP | 2570403 A1 | 3/2013 |
| FR | 2827599 A1 | 1/2003 |
| JP | 11-514361 A | 12/1999 |
| JP | 2010-530736 A | 9/2010 |
| JP | 5752239 B2 | 7/2015 |
| WO | 1997/14681 A1 | 4/1997 |
| WO | 1999/30696 A1 | 6/1999 |
| WO | 2007/058927 A1 | 5/2007 |
| WO | 2008/011476 A2 | 1/2008 |
| WO | 2008/074068 A1 | 6/2008 |
| WO | 2009/086303 A2 | 7/2009 |
| WO | 2009/134973 A1 | 11/2009 |
| WO | 2010/085514 A1 | 7/2010 |
| WO | 2010/088450 A2 | 8/2010 |
| WO | 2010/114881 A1 | 10/2010 |
| WO | 2013/118071 A1 | 8/2013 |
| WO | 2016/032569 A1 | 3/2016 |

OTHER PUBLICATIONS

STN registry record (RN# 1388744-24-8, entered date: Aug. 9, 2012).*
U.S. Appl. No. 15/507,228, filed Feb. 27, 2017, abandoned.
U.S. Appl. No. 16/258,060, filed Jan. 25, 2019, Granted.
U.S. Appl. No. 16/932,832, filed Jul. 20, 2020, Published.
CAS Registry No. 1388744-24-8, Benzamide, 4-(dimethylamino)-N-(2-methyl-8-quinolinyl). 1 page. Aug. 9, 2012.
CAS Registry No. 1883804-47-4, Benzamide, 4-(ethylamino)-N-(2-methyl-8-quinolinyl). 1 page, Mar. 21, 2016.
European Office Action for Application No. 21845832.1, dated Oct. 28, 2022, 7 pages.
International Search Report and Written Opinion for Application No. PCT/US2021/042235, dated Dec. 23, 2021, 10 pages.
Cornea et al., High-throughput FREI assay yields allosteric SERCA activators. J Biomol Screen. Jan. 2013;18(1):97-107.

(Continued)

*Primary Examiner* — Bong-Sook Baek
(74) *Attorney, Agent, or Firm* — McCarter & English, LLP; Steven G. Davis

(57) ABSTRACT

Provided herein are compounds of Formula I, pharmaceutical compositions thereof, and methods of their use for treating, preventing, or ameliorating one or more symptoms of a neurological disease, neurodegenerative disorder, or diabetes.

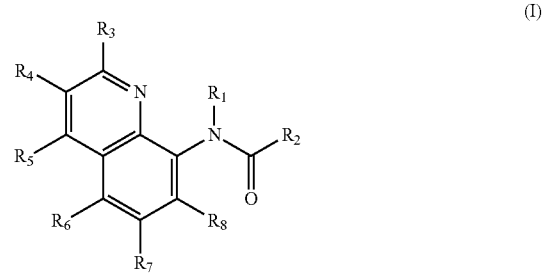

(I)

4 Claims, 4 Drawing Sheets

(56) References Cited

OTHER PUBLICATIONS

Dahl, A new target for Parkinson's disease: Small molecule SERCA activator CDN1163 ameliorates dyskinesia in 6-OHDA-lesioned rats. Bioorg Med Chem. Jan. 1, 2017;25(1):53-57.
Gruber et al., Discovery of enzyme modulators via high-throughput time-resolved FRET in living cells. J Biomol Screen. Feb. 2014;19(2):215-22.
Hetz et al., Disturbance of endoplasmic reticulum proteostasis in neurodegenerative diseases. Nat Rev Neurosci. Apr. 2014;15(4):233-49.
Kang et al., Small Molecular Allosteric Activator of the Sarco/Endoplasmic Reticulum Ca2+-ATPase (SERCA) Attenuates Diabetes and Metabolic Disorders. J Biol Chem. Mar. 4, 2016;291(10):5185-98.
Krajnak et al., A new target for Alzheimer's disease: A small molecule SERCA activator is neuroprotective in vitro and improves memory and cognition in APP/PS1 mice. Bioorg Med Chem Lett. May 15, 2018;28(9):1591-1594.
Lack et al., Targeting the binding function 3 (BF3) site of the human androgen receptor through virtual screening. J Med Chem. Dec. 22, 2011;54(24):8563-73.
Liu et al., SAR, cardiac myocytes protection activity and 3D-QSAR studies of salubrinal and its potent derivatives. Curr Med Chem. 2012;19(35):6072-9.
Munshi et al., Cytoprotective small molecule modulators of endoplasmic reticulum stress. Bioorg Med Chem. Jun. 1, 2016;24(11):2382-8.
Ong et al., Synthesis of bisquinolineepyrrole oligomide as G-quadruplex binding ligand. Tetrahedron. Apr. 24, 2012;68(27):5453-7.
PubChem, Accession No. AID 2314, Cycloheximide Counterscreen for Small Molecule Inhibitors of Shiga Toxin. 15 pages, Feb. 1, 2010.
PubChem, Accession No. CID 16016585, 4-Isopropoxy-N-(2-methylquinolin-8-yl)benzamide, 1 page, Apr. 2, 2007.
PubChem, Accession No. CID 16016591, 2-Ethoxy-N-(2-methylquinolin-8-yl)benzamide, 1 page, Apr. 2, 2007.
PubChem, Accession No. CID 16455930, 4-Chloro-N-(2-methylquinolin-8-yl)benzamide, 1 page, Jul. 30, 2007.
PubChem, Accession No. CID 16455975, 2-Methoxy-N-(2-methylquinolin-8-yl)benzamide, 1 page, Jul. 30, 2007.
PubChem, Accession No. CID 16475746, 4-Ethoxy-N-(2-methylquinolin-8-yl)benzamide, 1 page, Jul. 30, 2007.
PubChem, Accession No. CID 17010759, 4-Methoxy-N-(2-methylquinolin-8-yl)benzamide. 1 page, Nov. 13, 2007.
PubChem, Accession No. CID 17010761, 3-Chloro-N-(2-methylquinolin-8-yl)benzamide, 1 page, Nov. 13, 2007.
PubChem, Accession No. CID 17018402, 4-Bromo-N-(2-methylquinolin-8-yl)benzamide, 1 page, Nov. 13, 2007.
PubChem, Accession No. CID 17385424, 3-Bromo-N-(2-methylquinolin-8-yl)benzamide, 1 page, Nov. 13, 2007.
PubChem, Accession No. CID 17393560, 5-Chloro-N-(quinolin-8-yl)thiophene-2-carboxamide, 1 page, Nov. 13, 2007.
PubChem, Accession No. CID 17399709, 5-Methyl-N-(quinolin-8-yl)thiophene-2-carboxamide, 1 page, Nov. 13, 2007.
PubChem, Accession No. CID 25610351, 3-Methyl-N-(quinolin-8-yl)thiophene-2-carboxamide, 1 page, May 27, 2009.
PubChem, Accession No. CID 26123040, 4,5-Dibromo-N-quinolin-8-ylthiophene-2-carboxamide, 1 page, May 28, 2009.
PubChem, Accession No. CID 3161737, 3-Chloro-4-methoxy-N-(2-methylquinolin-8-yl)benzamide, 1 page, Aug. 10, 2005.
PubChem, Accession No. CID 3161759, 2-Chloro-N-(2-methylquinolin-8-yl)benzamide, 1 page, Aug. 10, 2005.
PubChem, Accession No. CID 41661472, 5-Bromo-N-(quinolin-8-yl)thiophene-2-carboxamide, 1 page, May 30, 2009.
PubChem, Accession No. CID 60227481, 4-(Dimethylamino)-N-(2-methylquinolin-8-yl)benzamide, 1 page, Oct. 18, 2012.
PubChem, Accession No. CID 62954642, 5-Bromo-N-(2-methylquinolin-8-yl)thiophene-2-carboxamide, 1 page, Oct. 22, 2012.
PubChem, Accession No. CID 6460550, N-(2-Methylquinolin-8-yl)-3-propan-2-yloxybenzamide, 1 page, Apr. 29, 2006.
PubChem, Accession No. CID 6460836, 2-Chloro-4-methyl-N-(2-methylquinolin-8-yl)benzamide, 1 page, Apr. 29, 2006.
PubChem, Accession No. CID 6463816, 2-Methoxy-3-methyl-N-(2-methylquinolin-8-yl)benzamide, 1 page, Apr. 29, 2006.
PubChem, Accession No. CID 6491457, N-(2-Methylquinolin-8-yl)thiophene-2- carboxamide, 1 page, Apr. 30, 2006.
PubChem, Accession No. CID 683655, N-Quinolin-8-ylthiophene-2-carboxamide, 1 page, Jul. 7, 2005.
PubChem, Accession No. CID 753092, 4-Tert-butyl-N-(2-methylquinolin-8-yl)benzamide, 1 page, Jul. 8, 2005.
PubChem, Accession No. CID 836753, 4-Propan-2-yloxy-N-quinolin-8-ylbenzamide, 1 page, Jul. 9, 2005.
Seprodi et al., HPLC Analysis, Modeling, and Biological Studies of Antiproliferative Heterocyclic Carboxamides. Peptides: The Wave of the Future. American Peptide Society, vol. 7, Lebl M., (Ed ). Chapter 12, pp. 805-806, (2001).
STN Accession No. 1360367-75-4, 3-Morpholineacetamide, N-[2-(3,5-dimethyl-1H-pyrazol-1-yl)-8-quinolinyl]. 1 page, Mar. 7, 2012.
STN Accession No. 360784-55-0, Benzamide, 2-bromo-N-[2-(3,5-dimethyl-1H-pyrazol-1-yl)-8-quinolinyl], 1 page, Oct. 8, 2001.
Yang et al., Design, synthesis and biological evaluation of quinoline amide derivatives as novel VEGFR-2 inhibitors. Bioorg Med Chem Lett. Nov. 15, 2010;20(22):6653-6.
International Search Report and Written Opinion for Application No. PCT/US2015/021742, dated Sep. 17, 2015, 25 pages.
STN Registry Record, RN# 1388744-24-8, dated Aug. 9, 2012.

* cited by examiner

QUINOLINES THAT MODULATE SERCA AND THEIR USE FOR TREATING DISEASE

CROSS-REFERENCE TO RELATED APPLICATIONS

This application is a Continuation-in-Part of U.S. application Ser. No. 16/932,832, filed on Jul. 20, 2020, the entire teachings of which are incorporated herein.

FIELD OF THE INVENTION

Provided herein are quinolines, pharmaceutical compositions thereof, and methods of their use for treating, preventing, or ameliorating one or more symptoms of a neurological or neurodegenerative disorder or diabetes. Also provided herein are methods of their use for modulating the activity of a sarcoplasmic/endoplasmic reticulum $Ca^{2+}$ ATPase (SERCA).

BACKGROUND OF THE INVENTION

The endoplasmic reticulum (ER) is an organelle, which plays an essential role in multiple cellular processes that are central for cell survival and normal cellular functions. Those vital cellular processes include intracellular calcium homeostasis, protein secretion, and lipid biosynthesis. Anelli et al., *EMBO J.* 2008, 27, 315-327; Pizzo et al., *Trends Cell Biol.* 2007, 17, 511-517; Ma et al., *J. Chem. Neuroanat.* 2004, 28, 51-65.

Perturbation of ER homeostasis leads to accumulation of unfolded protein in the ER, triggering an evolutionarily conserved response known as the unfolded protein response (UPR). Ron et al., *Nat. Rev. Mol. Cell Biol.* 2007, 8, 519-529; Malhotra et al., *Semin. Cell Dev. Biol.* 2007, 18, 716-731. Disturbances that lead to ER stress include, for example, disturbances in cellular redox regulation, glucose deprivation, aberration of calcium regulation in the ER, viral infection, high-fat diet, protein-inclusion-body diseases (e.g., chronic neurodegenerative diseases), and inclusion-body myositis. Kim et al., *Nat. Rev. Drug Dis.* 2008, 7, 1013-1030; Ma et al., *J. Chem. Neuroanat.* 2004, 28, 51-65; Ozcan et al., *Science* 2004, 306, 457-461; Frand et al., *Trends Cell Biol.* 2000, 10, 203-310. ER stress has been linked to a wide range of diseases, including neurodegeneration (e.g., Alzheimer's disease, Parkinson's disease, amyotrophic lateral sclerosis, polyglutamine disease, and prion disease), stroke, bipolar disorder, heart disease, atherosclerosis, cancer, diabetes (types 1 and 2), muscle degeneration, inflammatory diseases, and autoimmune disease. Kim et al., *Nat. Rev. Drug Dis.* 2008, 7, 1013-1030; Oyadomari et al., *Cell Death Differ.* 2004, 11, 381-389.

Sarcoplasmic/endoplasmic reticulum $Ca^{2+}$ ATPase (SERCA), is a major regulator of ER stress and glucose homeostasis in obesity. Park et al., *Proc. Natl. Acad. Sci. U.S.A.* 2010, 107, 19320-19325. Obesity disrupts intracellular $Ca^{2+}$ homeostasis and induces ER stress. Fu et al., *Nature* 2011, 473, 528-531. Chronic activation of ER stress has been implicated in the development of insulin resistance and diabetes in obesity. Hotamisligil, Cell 2010, 140, 900-917; Kim et al. *Nat. Rev. Drug Discov.* 2008, 7, 1013-1030. ER $Ca^{2+}$-homeostasis is found to be altered in small and non-small cell lung cancer cell lines. Bergner et al., *J. Exp. Clin. Cancer Res.* 2009, 28, 25. Restoration of $Ca^{2+}$ homeostasis via SERCA activation has been shown to alleviate dyskinesia in a model of Parkinson's disease. Dahl, *Bioorg. Med. Chem.* 2017, 25, 53-57. SERCA activation has also been shown to improve memory and coordination in a transgenic mouse model of Alzheimer's disease. Krajnak & Dahl, *Bioorg. Med. Chem Lett.* 2018, 28, 1591-1594. Therefore, there is a need for therapeutic agents capable of reducing ER stress or restoring ER homeostasis for treating ER stress-caused diseases.

SUMMARY OF THE INVENTION

Disclosed herein are SERCA modulators. Certain SERCA modulators, e.g., compounds C18, C19 and C20, have significantly improved pharmacokinetic properties compared with other SERCA modulators, e.g., compounds of Formula I in which $R^2$ is an amino substituted phenyl group, such as C18-C20, as measured by $C_{MAX}$, AUC and F(%) (see Table 6).

Provided herein is a method for treating, preventing, or ameliorating one or more symptoms of an endoplasmic reticulum stress-caused disease in a subject, comprising administering to the subject a compound of Formula I:

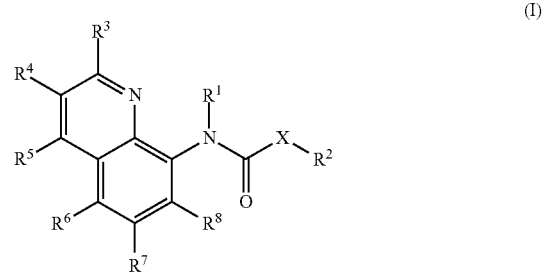

(I)

or an enantiomer, a mixture of enantiomers, a mixture of two or more diastereomers, or an isotopic variant thereof; or a pharmaceutically acceptable salt, solvate, hydrate, or prodrug thereof; wherein:

$R^1$ and $R^2$ are:
i. $R^1$ is (a) hydrogen; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or
(c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; and $R^2$ is hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or
ii. $R^1$ and $R^2$ together with the C and N atoms to which they are directly attached form heteroaryl or heterocyclyl;

$R^3$, $R^4$, $R^5$, $R^6$, $R^7$, and $R^8$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

X is a bond, —O—, —NR$^{1a}$—, C$_{1-6}$ alkylene, C$_{2-6}$ alkenylene, C$_{2-6}$ alkynylene, C$_{3-10}$ cycloalkylene, C$_{6-14}$ arylene, heteroarylene, or heterocyclylene; and each R$^{1a}$, R$^{1b}$, R$^{1c}$, and R$^{1d}$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^{1b}$ and R$^{1c}$ together with the N atom to which they are attached form heterocyclyl;

wherein each alkyl, alkylene, alkenyl, alkenylene, alkynyl, alkynylene, cycloalkyl, cycloalkylene, aryl, arylene, aralkyl, heteroaryl, heteroarylene, heterocyclyl, and heterocyclylene is optionally substituted with one or more, in one embodiment, one, two, three, or four, substituents Q, wherein each substituent Q is independently selected from (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c)—C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is further optionally substituted with one or more, in one embodiment, one, two, three, or four, substituents Q$^a$; or (iii) R$^b$ and R$^c$ together with the N atom to which they are attached form heterocyclyl, which is further optionally substituted with one or more, in one embodiment, one, two, three, or four, substituents Q$^a$;

wherein each Q$^a$ is independently selected from the group consisting of (a) oxo, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c)—C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

Also provided herein is a method for treating, preventing, or ameliorating one or more symptoms of an endoplasmic reticulum stress-caused disease in a subject, comprising administering to the subject a compound of Formula I, or an enantiomer, a mixture of enantiomers, a mixture of two or more diastereomers, or an isotopic variant thereof; or a pharmaceutically acceptable salt, solvate, hydrate, or prodrug thereof; wherein: R$_1$ is (a) hydrogen or (b) C$_{1-3}$ alkyl; R$_2$ is phenyl, 2-thienyl, 2-furyl, 2-benzothienyl, or 2-benzofuryl, wherein R$_2$ is optionally substituted with one to two substituents independently selected from halo, cyano, —O—(C$_1$-C$_4$ alkyl or haloalkyl), C$_1$-C$_4$ alkyl or haloalkyl, —N(CH$_3$)$_2$, and —NH—(C$_1$-C$_4$ alkyl) with the exception of F and NO$_2$; R$_3$ is CH$_3$ or H; and R$_4$, R$_5$, R$_6$, R$_7$, and R$_8$ are each independently (a) hydrogen, cyano, or halo; (b) C$_{1-4}$ alkyl, —O—(C$_1$-C$_4$ alkyl), or —N(CH$_3$)$_2$. In another aspect, R$_2$ is phenyl, 2-thienyl, 2-furyl, 2-benzothienyl, or 2-benzofuryl, wherein R$_2$ is optionally substituted with —N(CH$_3$)$_2$ or —NH—(C$_1$-C$_4$ alkyl) and the remainder of the variables are as just described in this paragraph. In another aspect, R$_2$ is phenyl optionally substituted with —N(CH$_3$)$_2$ or —NH—(C$_1$-C$_4$ alkyl); and the remainder of the variables are as just described in this paragraph.

Also provided herein is a method for treating, preventing, or ameliorating one or more symptoms of an endoplasmic reticulum stress-caused disease in a subject, comprising administering to the subject a compound of Formula V:

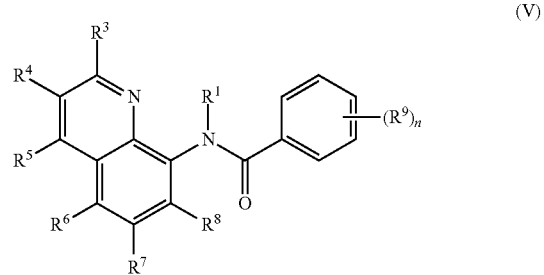

(V)

or an enantiomer, a mixture of enantiomers, a mixture of two or more diastereomers, or an isotopic variant thereof; or a pharmaceutically acceptable salt, solvate, hydrate, or prodrug thereof; wherein:

R$^1$ is (a) hydrogen; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c)—C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^3$, R$^4$, R$^5$, R$^6$, R$^7$, R$^8$, and R$^9$ are each independently (a) hydrogen, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c)—C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

each R$^{1a}$, R$^{1b}$, R$^{1c}$, and R$^{1d}$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^{1b}$ and R$^{1c}$ together with the N atom to which they are attached form heterocyclyl; and n is an integer of 0, 1, 2, 3, 4, or 5;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, wherein each substituent Q is independently selected from (a) oxo, cyano, halo, and nitro; (b)

$C_{1-6}$alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c)—C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is further optionally substituted with one or more, in one embodiment, one, two, three, or four, substituents $Q^a$; or (iii) $R^b$ and $R^c$ together with the N atom to which they are attached form heterocyclyl, which is further optionally substituted with one or more, in one embodiment, one, two, three, or four, substituents $Q^a$;

wherein each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c)—C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Furthermore, provided herein is a method for treating, preventing, or ameliorating one or more symptoms of a disorder, disease, or condition mediated by a sarcoplasmic/endoplasmic reticulum calcium ATP-ase (SERCA) in a subject, comprising administering to the subject a compound of Formula I, or an enantiomer, a mixture of enantiomers, a mixture of two or more diastereomers, or an isotopic variant thereof; or a pharmaceutically acceptable salt, solvate, hydrate, or prodrug thereof.

Provided herein is a method for treating, preventing, or ameliorating one or more symptoms of diabetes in a subject, comprising administering to the subject a compound of Formula I, or an enantiomer, a mixture of enantiomers, a mixture of two or more diastereomers, or an isotopic variant thereof; or a pharmaceutically acceptable salt, solvate, hydrate, or prodrug thereof.

Provided herein is a method for increasing glucose tolerance in a subject, comprising administering to the subject a compound of Formula I, or an enantiomer, a mixture of enantiomers, a mixture of two or more diastereomers, or an isotopic variant thereof; or a pharmaceutically acceptable salt, solvate, hydrate, or prodrug thereof.

Provided herein is a method for treating, preventing, or ameliorating one or more symptoms of Alzheimer's disease in a subject, comprising administering to the subject a compound of Formula I, or an enantiomer, a mixture of enantiomers, a mixture of two or more diastereomers, or an isotopic variant thereof; or a pharmaceutically acceptable salt, solvate, hydrate, or prodrug thereof.

Provided herein is a method for treating, preventing, or ameliorating one or more symptoms of Parkinson's disease in a subject, comprising administering to the subject a compound of Formula I, or an enantiomer, a mixture of enantiomers, a mixture of two or more diastereomers, or an isotopic variant thereof; or a pharmaceutically acceptable salt, solvate, hydrate, or prodrug thereof.

Provided herein is a method for reducing stress in an ER, comprising contacting the ER with a compound of Formula I, or an enantiomer, a mixture of enantiomers, a mixture of two or more diastereomers, or an isotopic variant thereof; or a pharmaceutically acceptable salt, solvate, hydrate, or prodrug thereof.

Provided herein is a method for restoring or maintaining homeostasis in an ER, comprising contacting the ER with a compound of Formula I, or an enantiomer, a mixture of enantiomers, a mixture of two or more diastereomers, or an isotopic variant thereof; or a pharmaceutically acceptable salt, solvate, hydrate, or prodrug thereof.

Provided herein is a method for increasing the $Ca^{2+}$ concentration of an ER, comprising contacting the ER with a compound of Formula I, or an enantiomer, a mixture of enantiomers, a mixture of two or more diastereomers, or an isotopic variant thereof; or a pharmaceutically acceptable salt, solvate, hydrate, or prodrug thereof.

Provided herein is a method for modulating the activity of a SERCA, comprising contacting the SERCA with a compound of Formula I, or an enantiomer, a mixture of enantiomers, a mixture of two or more diastereomers, or an isotopic variant thereof; or a pharmaceutically acceptable salt, solvate, hydrate, or prodrug thereof.

DETAILED DESCRIPTION

Figure 1:
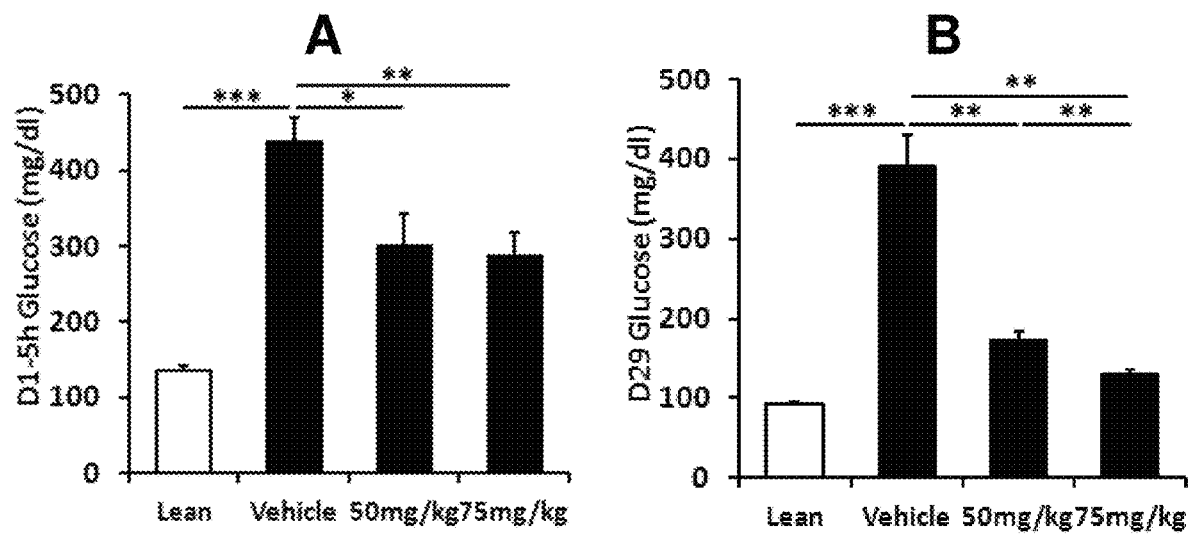
FIG. 1 shows the effect of compound A12 on blood glucose levels in ob/ob mice treated with 50 mg/kg and 75 mg/kg of compound A12 after 1 (A) and 21 (B) days.
Figure 2:
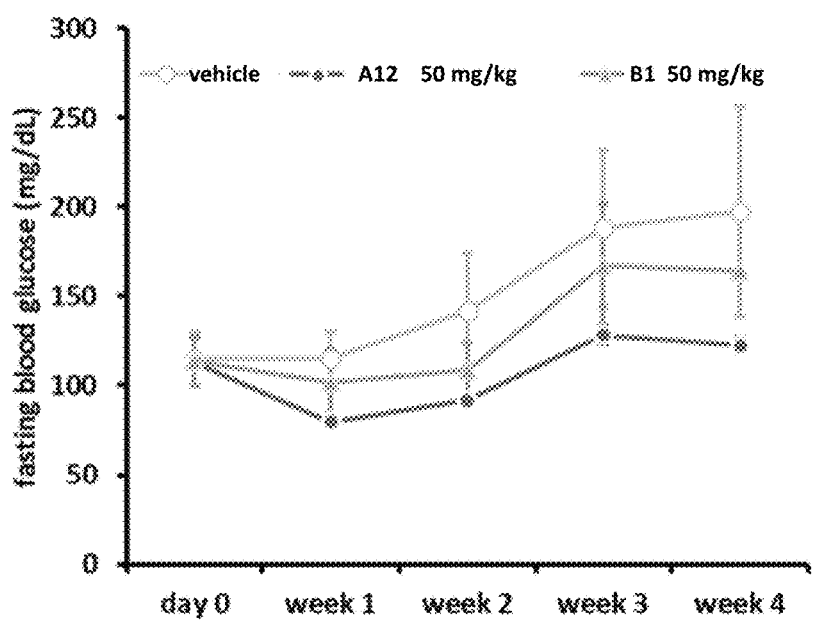
FIG. 2 shows the effect of compounds A12 and B1 on blood glucose levels in ob/ob mice treated daily with 50 mg/kg of compound A12 or B1 for 4 weeks (○—Vehicle; ●—Cmpd. A12; ▲—Cmpd. Bi). ●

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject. In one embodiment, the subject is a human.

The terms "treat," "treating," and "treatment" are meant to include alleviating or abrogating a disorder, disease, or condition, or one or more symptoms of the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" is meant to include the amount of a compound that, when administered, is sufficient to prevent development of, or alleviate to some extent, one or more symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st Edition, Lippincott Williams & Wilkins: Philadelphia, Pa., 2005; *Handbook of Pharmaceutical Excipients*, 7th Edition, Rowe et al., Eds., The Pharmaceutical Press and the American Pharmaceutical Association: 2012; *Handbook of Pharmaceutical Additives*, 3rd Edition, Ash and Ash Eds., Gower Publishing Company: 2007; and Pharmaceutical Preformulation and Formulation, 2nd Edition, Gibson Ed., CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer of a compound described herein.

The terms "drug," "therapeutic agent," and "chemotherapeutic agent" refer to a compound or a pharmaceutical composition thereof, which is administered to a subject for treating, preventing, or ameliorating one or more symptoms of a disorder, disease, or condition.

The term "endoplasmic reticulum stress" or "ER stress" refers to perturbation of endoplasmic reticulum homeostasis, e.g., perturbation of the protein folding functionality of the endoplasmic reticulum.

The term "ER stress disorder, disease, or condition," "ER stress-caused disorder, disease, or condition," "a disorder, disease, or condition caused by ER stress," or "a disorder, disease, or condition associated with ER stress" refers to a disorder, disease, or condition resulted from perturbation of ER homeostasis. In particular, an ER stress disorder, disease, or condition is one in which reduction of ER stress results in some effect on the underlying disorder, disease, or condition, e.g., an ER stress modulator results in some improvement in at least some of patients being treated.

The term "naturally occurring" or "native" when used in connection with a biological material, such as a nucleic acid (e.g., a DNA or RNA), a polypeptide, and a host cell, refers to a material which is found in nature and is not manipulated by man. Similarly, "non-naturally occurring" or "non-native" refers to a material that is not found in nature or that has been structurally modified or synthesized by man.

The term "SERCA" or "sarco(endo)plasmic reticulum $Ca^{2+}$ ATPase" refers to a sarcoplasmic/endoplasmic reticulum $Ca^{2+}$ ATPase or a variant thereof. The term "SERCA variant" is intended to include proteins substantially homologous to a native SERCA, i.e., proteins having one or more naturally or non-naturally occurring amino acid deletions, insertions, or substitutions (e.g., SERCA derivatives, homologs, and fragments), as compared to the amino acid sequence of a native SERCA. The amino acid sequence of a SERCA variant is at least about 80% identical, at least about 90% identical, or at least about 95% identical to a native SERCA. SERCA enzymes are classified into at least three classes: SERCA1, SERCA2, and SERCA3. Stutzmann et al., *Pharmacol. Rev.* 2011, 63, 700-727; Andersen et al., *Acta Physiol. Scand.* Suppl. 1998, 643, 45-54. Class I includes SERCA1a and SERCA1b. Class II includes SERCA2a and SERCA2b. Class III includes SERCA3a, SERCA3b, and SERCA3c.

The terms "SERCA-mediated disorder, disease, or condition" and "a disorder, disease, or condition mediated by SERCA" refer to a disorder, disease, or condition in which modulation of a SERCA activity results in some effect on the underlying disorder, disease, or condition, e.g., a SERCA agonist results in some improvement in at least some of patients being treated.

The term "alkyl" refers to a linear or branched saturated monovalent hydrocarbon radical, wherein the alkyl is optionally substituted with one or more substituents Q as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkenyl" refers to a linear or branched monovalent hydrocarbon radical, which contains one or more, in one embodiment, one, two, three, four, or five, in another embodiment, one, carbon-carbon double bond(s). In certain embodiments, the alkenyl is optionally substituted with one or more substituents Q as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one, two, three, four, or five, in another embodiment, one, carbon-carbon triple bond(s). In certain embodiments, the alkynyl is optionally substituted with one or more substituents Q as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic saturated or non-aromatic unsaturated, bridged or non-bridged monovalent hydrocarbon radical, which is optionally substituted with one or more substituents Q as described herein. In certain embodiments, the cycloalkyl is a cyclic saturated bridged or non-bridged monovalent hydrocarbon radical. In certain embodiments, the cycloalkyl has from 3 to 20 ($C_{3-20}$), from 3 to 15 ($C_{3-15}$), from 3 to 10 ($C_3$-10), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and ter-phenyl. In certain embodiments, the term "aryl" refers to a bicyclic or tricyclic carbon ring, where one of the rings is aromatic and the others of which may be saturated, partially unsaturated, or aromatic, for example, dihydronaphthyl, indenyl, indanyl, or tetrahydronaphthyl (tetralinyl). In certain embodiments, the aryl is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 1-phenylethyl, 2-phenylethyl, and 3-phenylpropyl. In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each of which is independently selected from O, S, N, and P, in the ring. A heteroaryl group is bonded to the rest of a molecule through its aromatic ring. Each ring of a heteroaryl group can contain one or two O atoms, one or two S atoms, one to four N atoms, and/or one or two P atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each of which is independently selected from O, S, N, and P; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. A heterocyclyl group is bonded to the rest of a molecule through its non-aromatic ring. In certain embodiments, the heterocyclyl is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclic groups include, but are not limited to, azepinyl, benzodioxanyl, benzodioxolyl, benzofuranonyl, benzofuranyl, benzopyranonyl, benzopyranyl, benzotetrahydrofuranyl, benzotetrahydrothienyl, benzothiopyranyl, benzoxazinyl, O-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "halogen", "halide" or "halo" refers to fluorine, chlorine, bromine, and/or iodine.

The term "optionally substituted" is intended to mean that a group or substituent, such as an alkyl, alkenyl, alkynyl, cycloalkyl, aryl, aralkyl, heteroaryl, and heterocyclyl group, may be substituted with one or more substituents Q, each of which is independently selected from, e.g., (a) oxo (=O), cyano (—CN), halo, and nitro (—NO$_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, four, or five, substituents $Q^a$; and c)—C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heteroaryl or heterocyclyl, each of which is optionally substituted with one or more, in one embodiment, one, two, three, or four, substituents $Q^a$. As used herein, all groups described herein that can be substituted are "optionally substituted," unless otherwise specified.

In one embodiment, each substituent $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c)—C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —P(O)R$^e$R$^h$, —P(O)(OR$^e$)R$^h$, —P(O)(OR$^e$)(OR$^h$), —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) R$^f$ and R$^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the two enantiomers in question.

In describing an optically active compound, the prefixes R and S are used to denote the absolute configuration of the optically active compound about its chiral center(s). The (+) and (−) are used to denote the optical rotation of an optically active compound, that is, the direction in which a plane of polarized light is rotated by the optically active compound. The (−) prefix indicates that an optically active compound is levorotatory, that is, the compound rotates the plane of polarized light to the left or counterclockwise. The (+) prefix indicates that an optically active compound is dextrorotatory, that is, the compound rotates the plane of polarized light to the right or clockwise. However, the sign of optical rotation, (+) and (−), is not related to the absolute configuration of a compound, R and S.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I) It will be understood that, in a compound as provided herein, any hydrogen can be $^2$H, for example, or any carbon can be $^{13}$C, for example, or any nitrogen can be $^{15}$N, for example, or any oxygen can be $^{18}$O, for example, where feasible according to the judgment of one of skill. In certain embodiments, an "isotopic variant" of a compound contains unnatural proportions of deuterium (D).

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an enantiomer, a mixture of enantiomers, a mixture of two or more diastereomers, or an isotopic variant thereof; or a pharmaceutically acceptable salt, solvate, hydrate, or prodrug thereof" has the same meaning as the phrase "(i) an enantiomer, a mixture of enantiomers, a mixture of two or more diastereomers, or an isotopic variant of the compound referenced therein; (ii) a pharmaceutically acceptable salt, solvate, hydrate, or prodrug of the compound referenced therein; or (iii) a pharmaceutically acceptable salt, solvate, hydrate, or prodrug of an enantiomer, a mixture of enantiomers, a mixture of two or more diastereomers, or an isotopic variant of the compound referenced therein."

In one embodiment, provided herein is a compound of Formula (I) or an enantiomer, a mixture of enantiomers, a mixture of two or more diastereomers, or an isotopic variant thereof; or a pharmaceutically acceptable salt, solvate, hydrate, or prodrug thereof; wherein the variables are as described above. In another embodiment, provided herein is a compound of Formula (V) or an enantiomer, a mixture of enantiomers, a mixture of two or more diastereomers, or an isotopic variant thereof; or a pharmaceutically acceptable salt, solvate, hydrate, or prodrug thereof; wherein the variables are as described above. In yet another embodiment, provided herein is a compound selected from the group consisting of:

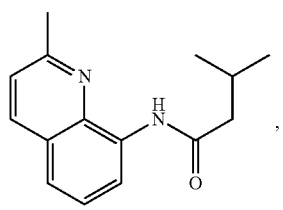

A1

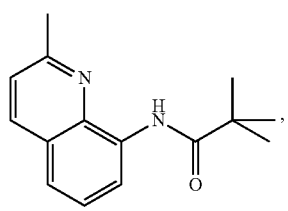

A2

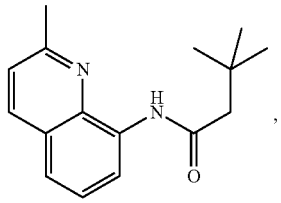

A3

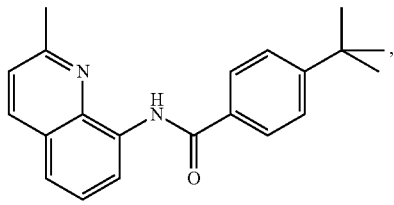

A4

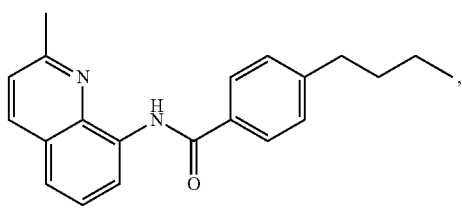

A5

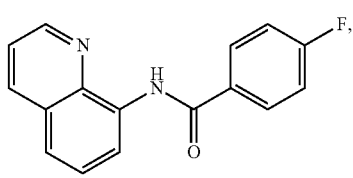

A6

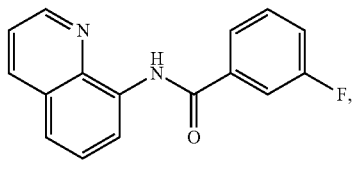

A7

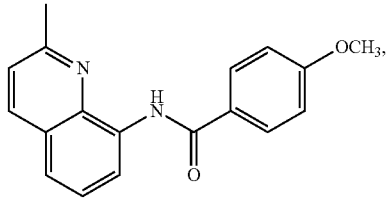

A8

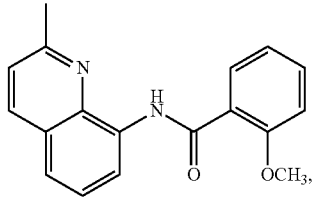

A9

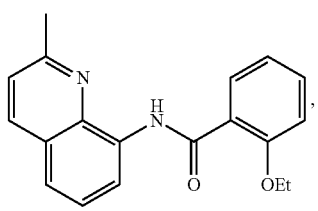

A10

-continued

A11

A12

A13

A14

A15

A16

A17

A18

A19

A20

A21

A22

A23

A24

A25

A26
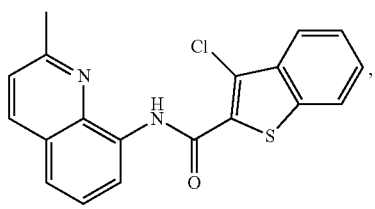

A27
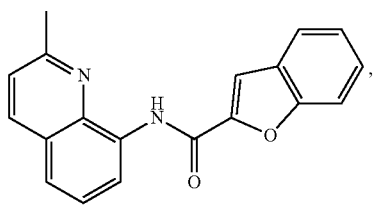

A28
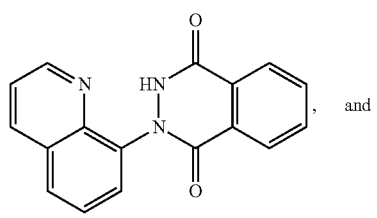, and

A29
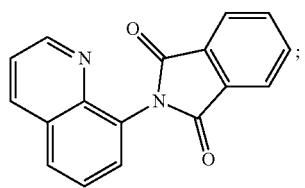;

and isotopic variants thereof; and pharmaceutically acceptable salts, solvates, hydrates, and prodrugs thereof.

In another embodiment, provided herein is a compound selected from the group consisting of:

B1
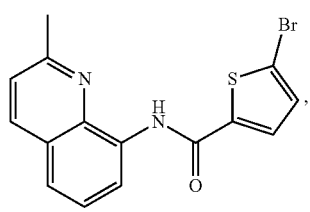,

B2
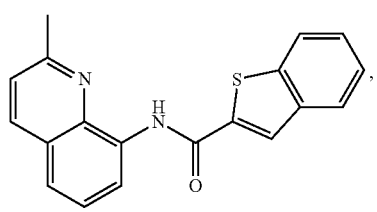,

B3
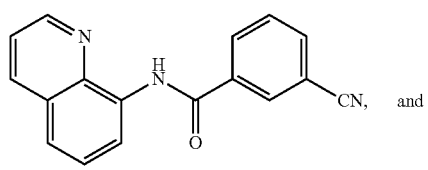, and

B4
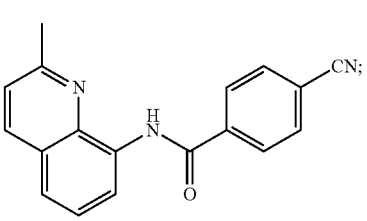

and isotopic variants thereof; and pharmaceutically acceptable salts, solvates, hydrates, and prodrugs thereof.

In yet another embodiment, provided herein is a compound selected from the group consisting of:

C1
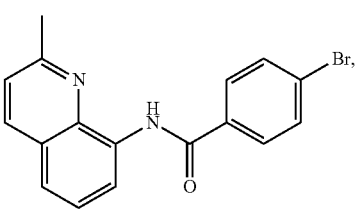

C2
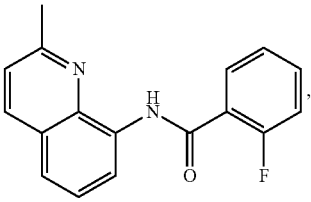,

C3
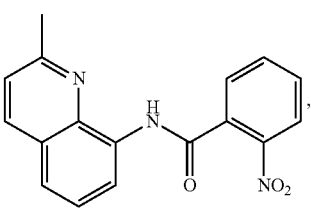,

C4
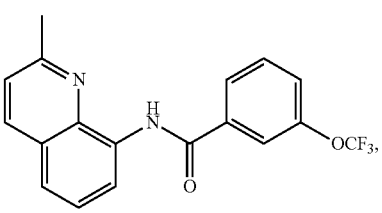,

C5
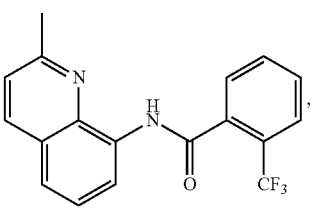,

| | |
|---|---|
| C6 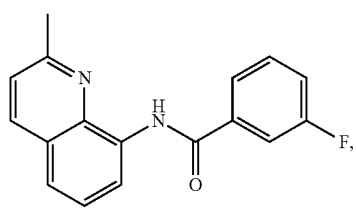 | C13 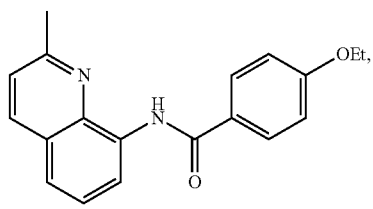 |
| C7 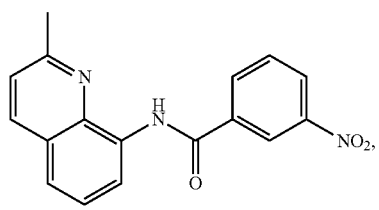 | C14 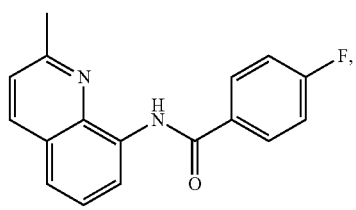 |
| C8 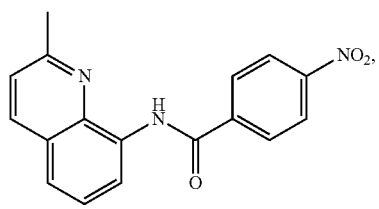 | C15 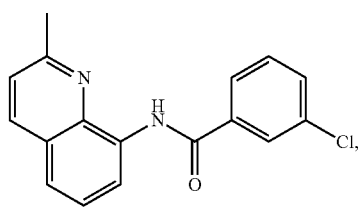 |
| C9 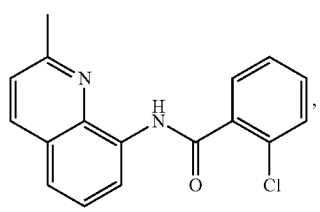 | C16 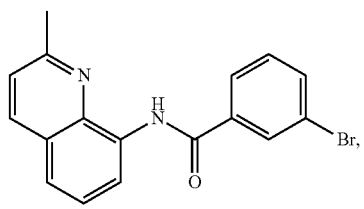 |
| C10 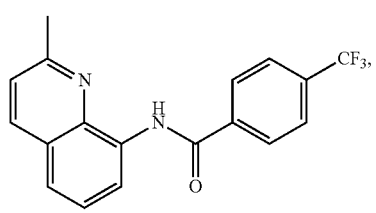 | C17 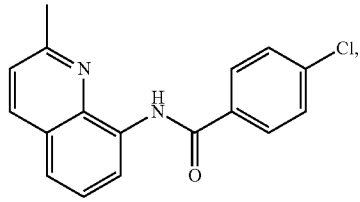 |
| C11 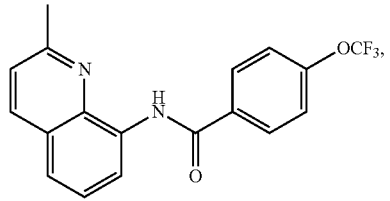 | C18 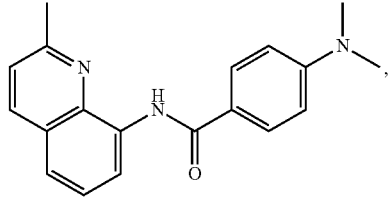 |
| C12 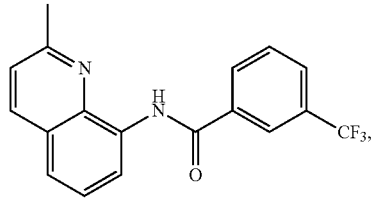 | C19 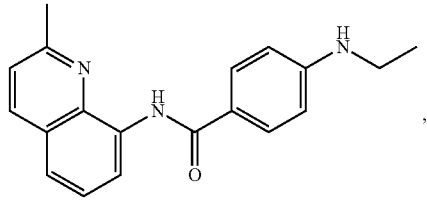 |

-continued

C20
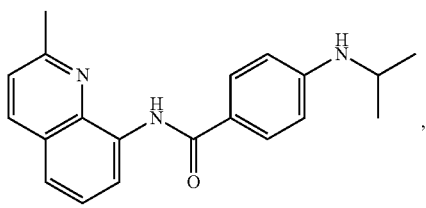,

C21
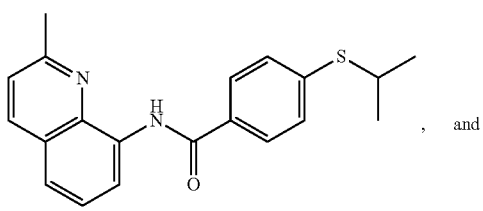, and

C22
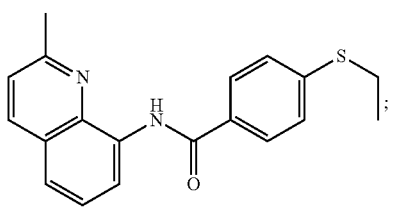;

and isotopic variants thereof; and pharmaceutically acceptable salts, solvates, hydrates, and prodrugs thereof.

In yet another embodiment, provided herein is a compound selected from the group consisting of:

E1
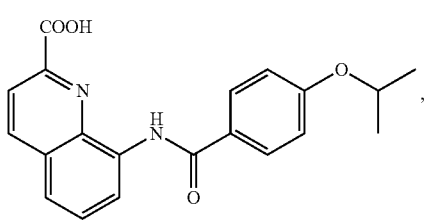,

E2
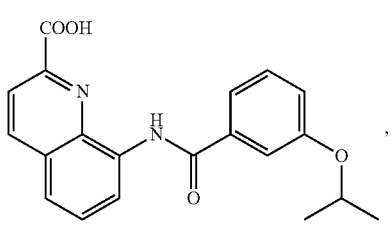,

E3
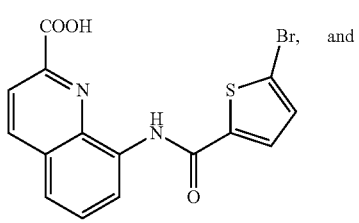

-continued

E4
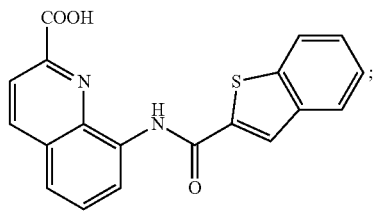;

and isotopic variants thereof; and pharmaceutically acceptable salts, solvates, hydrates, and prodrugs thereof.

In yet another embodiment, provided herein is a compound selected from the group consisting of:

F1
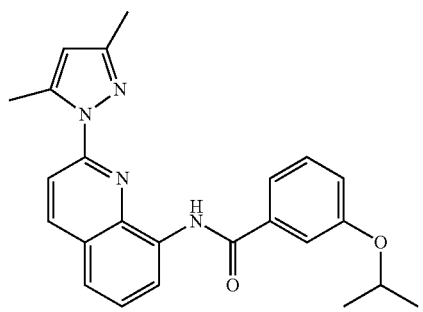,

F2
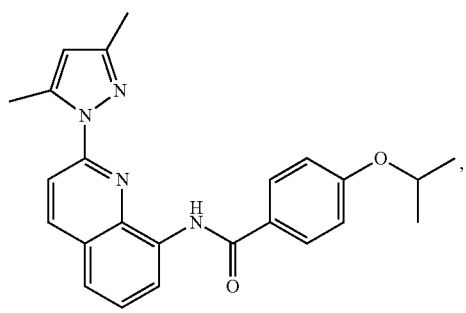,

F3
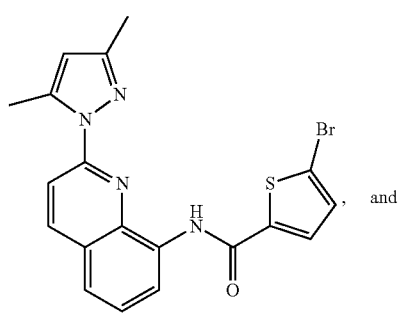, and

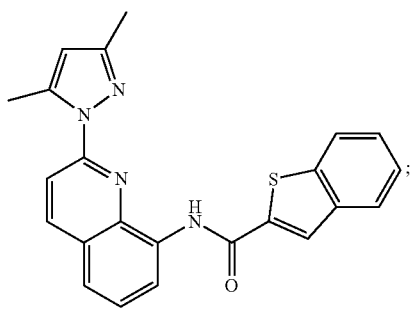

F4 and isotopic variants thereof; and pharmaceutically acceptable salts, solvates, hydrates, and prodrugs thereof.

In yet another embodiment, provided herein is a compound selected from the group consisting of:

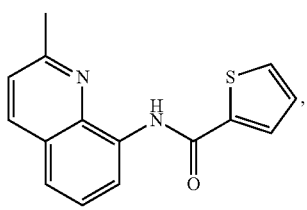

G1, G2, G3, G4, G5

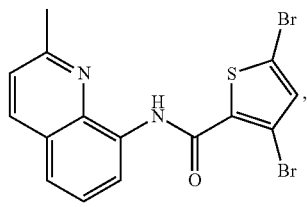

G6, G7, G8 and isotopic variants thereof; and pharmaceutically acceptable salts, solvates, hydrates, and prodrugs thereof.

In still another embodiment, provided herein is a compound selected from the group consisting of:

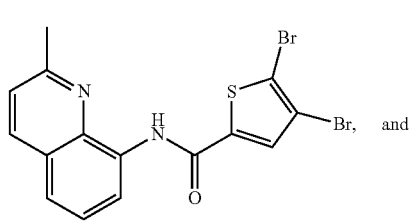

H1, H2

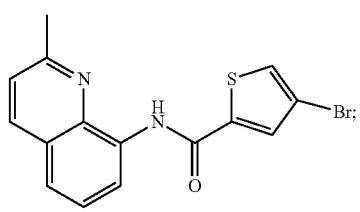

H3, H4

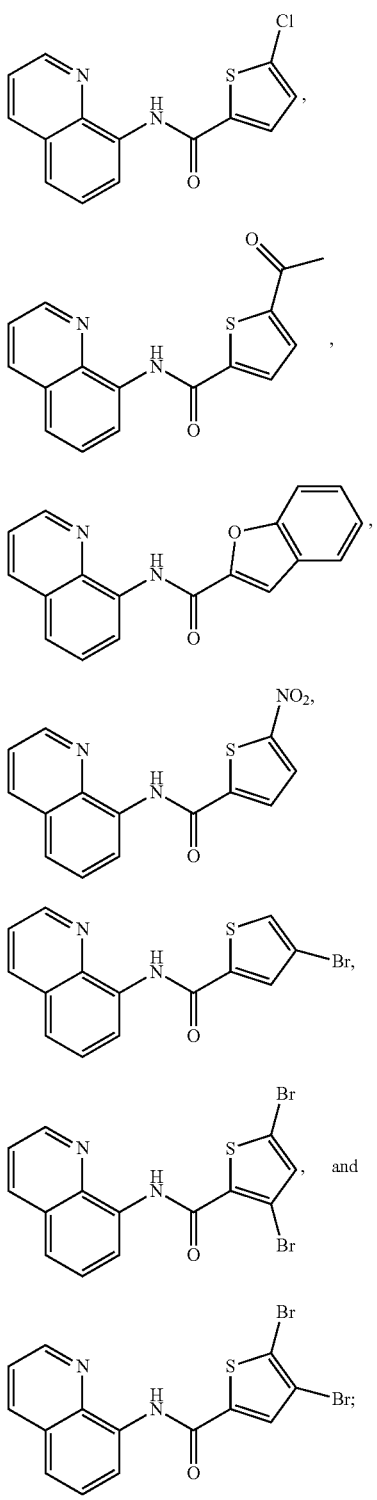

and isotopic variants thereof; and pharmaceutically acceptable salts, solvates, hydrates, and prodrugs thereof.

In certain embodiments, the compounds provided herein show activity as agonists of a SERCA. In certain embodiments, the compounds provided herein show activity as allosteric SERCA modulators. In certain embodiments, the compounds provided herein show activity as agonists of a SERCA2b. In certain embodiments, the compounds provided herein show activity as allosteric SERCA2b modulators.

In certain embodiments, the compounds provided herein show activity in reducing ER stress. In certain embodiments, the compounds provided herein show activity in increasing the $Ca^{2+}$ concentration of an ER.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When a compound provided herein contains an acidic or basic moiety, it may also be provided as a pharmaceutically acceptable salt (See, Berge et al., *J. Pharm. Sci.* 1977, 66, 1-19; and "*Handbook of Pharmaceutical Salts, Properties, and Use,*" Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, include, but are not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

A compound provided herein may also be provided as a prodrug, which is a functional derivative of the compound, for example, of Formula V, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, Progress in Drug Research 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neurophar-macol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

The compounds provided herein can be prepared, isolated, or obtained by any methods known to one of skill in the art, and the following examples are only representative and do not exclude other related procedures.

In one embodiment, for example, a compound of Formula I is prepared, as shown in Scheme I, via a coupling reaction of an amine I-1 with compound I-2 having a leaving group L, optionally in the presence of a coupling reagent, to form compound I. In certain embodiments, L is hydroxyl or halo. In certain embodiments, L is hydroxyl, fluoro, chloro, bromo, or iodo.

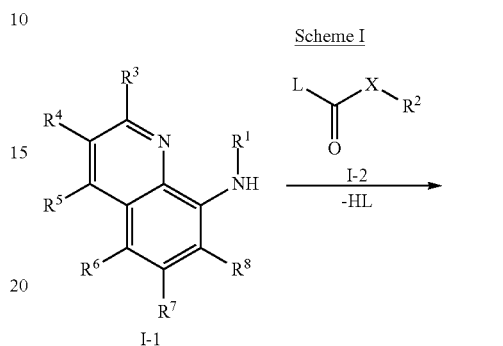

Scheme I

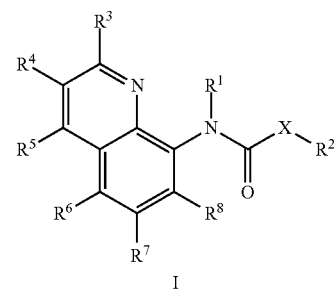

I

In another embodiment, for example, a compound of Formula V is prepared, as shown in Scheme Ia, via a coupling reaction of an amine I-1 with compound V-2 having a leaving group L, optionally in the presence of a coupling reagent, to form compound V. In certain embodiments, L is hydroxyl or halo. In certain embodiments, L is hydroxyl, fluoro, chloro, bromo, or iodo.

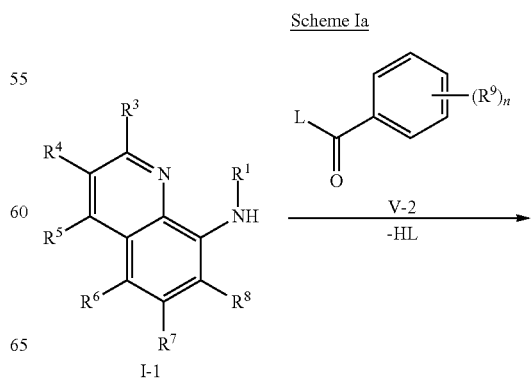

Scheme Ia

-continued

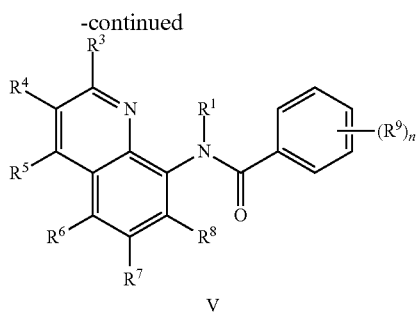

V

Examples of suitable coupling reagents include, but are not limited to, carbodiimides (e.g., N-(3-dimethylaminopropyl)-N'-ethylcarbodiimide (EDC), N-(3-dimethylaminopropyl)-N'-ethylcarbodiimide hydrochloride (EDC hydrochloride), 1-[3-(dimethylamino)propyl]-3-ethylcarbodiimide methiodide (EDC methiodide), 1-cyclohexyl-3-(2-morpholinoethyl)carbodiimide metho-p-toluenesulfonate, N,N'-diisopropylcarbodiimide (DIC), and 1,3-dicyclohexylcarbodiimide (DCC)), 1,1'-carbonyldiimidazole (CDI), bis(2-oxo-3-oxazolidinyl)phosphinic chloride (BOP-Cl), 2-chloro-1,3-dimethylimidium hexafluorophosphate (CIP), bromotris(dimethylamino)phosphonium hexafluorophosphate, bromotripyrrolidinophosphonium hexafluorophosphate (PyBroP), 0-(7-azabenzotriazol-1-yl)-N,N,N',N'-tetramethyluronium hexafluorophosphate (HATU), 0-(7-azabenzotriazol-1-yl)-N,N,N',N'-tetramethyluronium tetrafluoroborate (TATU), (7-azabenzotriazol-1-yloxy)tripyrrolidinophosphoniumhexafluorophosphate (PyAOP), (benzotriazol-1-yloxy)tripyrrolidinophosphonium hexafluorophosphate (PyBOP), (benzotriazol-1-yloxy)tris(dimethylamino)phosphonium hexafluorophosphate (BOP reagent), N,N,N',N'-tetramethyl-O-(1H-benzotriazol-1-yl)uronium hexafluorophosphate (HBTU), O-(benzotriazol-1-yl)-N,N,N',N'-tetramethyluronium tetrafluoroborate (TBTU), O-(benzotriazol-1-yl)-N,N,N',N'-bis(tetramethylene)uronium hexafluorophosphate (HBPyU), O-(benzotriazol-1-yl)-N,N,N',N'-bis(pentamethylene)uronium hexafluorophosphate, acetic anhydride, $SOCl_2$, $PCl_3$, $POCl_3$, $PCl_5$, and mixtures thereof.

In one embodiment, provided herein is a pharmaceutical composition comprising the compound provided herein, including a compound of Formula I, or an enantiomer, a mixture of enantiomers, a mixture of two or more diastereomers, or an isotopic variant thereof; or a pharmaceutically acceptable salt, solvate, hydrate, or prodrug thereof; and a pharmaceutically acceptable excipient.

The disclosed compounds can be administered to a patient in a variety of forms depending on the selected route of administration, as will be understood by those skilled in the art. The disclosed compounds may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The disclosed compounds can be suitably formulated into pharmaceutical compositions for administration to a subject. The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5th Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a disclosed compound may be incorporated with an excipient and used in the form of ingestible tablets, buccal tablets, troches, capsules, elixirs, suspensions, syrups, wafers, and the like.

Typically for parenteral administration, solutions of a compound used in the disclosed methods can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound used in the disclosed methods for the extemporaneous preparation of sterile injectable solutions or dispersions are appropriate.

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

In one embodiment, provided herein is a method for treating, preventing, or ameliorating one or more symptoms of a disorder, disease, or condition mediated by a SERCA in a subject, comprising administering to the subject a therapeutically effective amount of a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

In certain embodiments, the disorder, disease, or condition mediated by a SERCA is a disorder, disease, or condition mediated by a SERCA2a. In certain embodiments, the disorder, disease, or condition mediated by a SERCA is a disorder, disease, or condition mediated by a SERCA2b.

In certain embodiments, the disorders, diseases, and conditions mediated by a SERCA is a cardiovascular disease, cancer, diabetes, an inflammatory disease, a metabolic disease, or a neurological disease. In certain embodiments, the disorders, diseases, and conditions mediated by a SERCA is a heart disease, stroke, stenosis, restenosis, a disease associated with vascular smooth muscle cell proliferation, a disease associated with neointima formation, a disease associated with calcineurin PP2B, a disease associated with NFAT, arteriovenous fistula failure, a cardiac disease, a disease associated with a cardiac disease, urinary incontinence, cancer, asthma, pulmonary hypertension, chronic obstructive pulmonary disease, diabetes, a neurodegenerative disease, bipolar disorder, atherosclerosis, muscle degeneration, or an autoimmune disease.

In yet another embodiment, provided herein is a method for treating, preventing, or ameliorating one or more symptoms of diabetes in a subject, comprising administering to the subject a therapeutically effective amount of a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof. In one embodiment, the diabetes is type 1. In one embodiment, the diabetes is type 2.

In yet another embodiment, provided herein is a method for increasing glucose tolerance in a subject, comprising administering to the subject a therapeutically effective amount of a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

In yet another embodiment, provided herein is a method for treating, preventing, or ameliorating one or more symptoms of hepatosteatosis in a subject, comprising administering to the subject a therapeutically effective amount of a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

In yet another embodiment, provided herein is a method for treating, preventing, or ameliorating one or more symptoms of obesity in a subject, comprising administering to the subject a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

In still another embodiment, provided herein is a method for promoting thermogenesis in a subject, comprising administering to the subject a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

In certain embodiments, the subject is a mammal. In certain embodiments, the subject is a human. In certain embodiments, the subject is a primate other than a human, a farm animal such as cattle, a sport animal, or a pet such as a horse, dog, or cat.

The disorders, diseases, or conditions treatable with a compound provided herein, include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period.

In the treatment, prevention, or amelioration of one or more symptoms of the disorders, diseases, or conditions described herein, an appropriate dosage level generally is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

For oral administration, the pharmaceutical compositions provided herein can be formulated in the form of tablets containing from about 1.0 to about 1,000 mg of the active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The pharmaceutical compositions can be administered on a regimen of 1 to 4 times per day, including once, twice, three times, and four times per day.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In one embodiment, provided herein is a method for reducing stress in an ER, comprising contacting the ER with an effective amount of a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof. In one embodiment, the ER stress is resulted from the perturbation of ER $Ca^{2+}$ homeostasis.

In yet another embodiment, provided herein is a method for restoring or maintaining homeostasis in an ER, comprising contacting the ER with an effective amount of a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

In yet another embodiment, provided herein is a method for increasing the $Ca^{2+}$ concentration of an ER, comprising contacting the ER with an effective amount of a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

In yet another embodiment, provided herein is a method for modulating the activity of a SERCA, comprising contacting the SERCA with an effective amount of a compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof.

In certain embodiments, the SERCA is SERCA1. In certain embodiments, the SERCA is SERCA2. In certain embodiments, the SERCA is SERCA3.

In certain embodiments, the SERCA is SERCA1a. In certain embodiments, the SERCA is SERCA1b. In certain embodiments, the SERCA is SERCA2a. In certain embodiments, the SERCA is SERCA2b. In certain embodiments, the SERCA is SERCA3a. In certain embodiments, the SERCA is SERCA3b. In certain embodiments, the SERCA is SERCA3c.

The compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof; can also be combined or used in combination with other agents or therapies useful in the treatment, prevention, or amelioration of one or more symptoms of the disorders, diseases, or conditions for which the compounds provided herein are useful.

Suitable other therapeutic agents can also include, but are not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) antidiabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

In certain embodiments, the other therapies that may be used in combination with the compounds provided herein include, but are not limited to, surgery, endocrine therapy, biologic response modifiers (e.g., interferons, interleukins, and tumor necrosis factor (TNF)), hyperthermia and cryotherapy, and agents to attenuate any adverse effects (e.g., antiemetics).

Such other agents, or drugs, can be administered, by a route and in an amount commonly used therefor, simultaneously or sequentially with the compound provided herein, e.g., a compound of Formula I, or an enantiomer, a mixture of enantiomers, a mixture of two or more diastereomers, or an isotopic variant thereof; or a pharmaceutically acceptable salt, solvate, hydrate, or prodrug thereof. When a compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to a compound provided herein.

EXAMPLES

The disclosure will be further understood by the following non-limiting examples.

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); M (molar); mM (millimolar); µM (micromolar); mol (moles); mmol (millimoles); hr or hrs (hour or hours); and min (minutes).

For all of the following examples, standard procedures and methods known to those skilled in the art can be utilized. Unless otherwise indicated, all temperatures are expressed in ° C. (degrees Centigrade). All procedures are conducted at room temperature unless otherwise noted.

Biological Assays

ER Stress Cell Survival Assay

CSM14.1 cells were maintained in Complete Medium at 32° C.; wherein the Complete Medium contained Dulbecco's modified eagle medium (DMEM) with 10% fetal bovine serum (FSB), 1% L-glutamine, 100 IU/mL penicillin, and 100 µg/mL streptomycin. The cells were recovered from cultures by trypsinization and then seeded in 384 well plates (Greiner #781098) at a concentration of 1,000 cells/well in 20 µL of DMEM Assay Medium, wherein the DMEM Assay Medium contained 2% FBS, 100 IU/mL penicillin, and 100 µg/mL streptomycin. Seeding was performed using a MultiDrop Combi reagent broadcaster. The plates were incubated overnight at 32° C.

A test compound was prepared by 2-fold serial dilution in 100% DMSO using a BIOMEK® 2000 liquid handler (Beckman Coulter). A dose-response curve containing 10 concentrations of the test compound was obtained. Using a BIOMEK® FX liquid handler (Beckman Coulter), 2.5 µL of the test compound was transferred from the 100% DMSO serial dilution plate to an intermediate plate containing 47.5 µL of DMEM Assay Medium containing 2% FBS, 100 IU/mL penicillin, and 100 µg/mL streptomycin and mixed. To reduce or eliminate the interference from the compound's precipitation, 6 µL of the diluted compound was immediately transferred to the assay plate to achieve a high compound concentration of 100 µM in 99% DMEM Assay Medium and 1% DMSO. After the assay plates were incubated for 2 hrs, 4 µL of 112.5 µM thapsigargin (TG) (DMSO stock diluted into Assay TC Medium) was dispensed into each testing well with a MultiDrop Combi reagent broadcaster for a final concentration of about 15 µM TG. The tissue culture media (4 µL) containing vehicle only was transferred manually to each control cell using a 16 channel electronic pipette. After the plates were incubated overnight (about 16 to 24 hrs), CELLTITER-GLO® (Promega) (16 µL) was added to all wells and luminescence was measured. High luminescence indicates cell survival.

Alternatively, a test compound was tested at a single compound concentration (e.g., 2 µM) to determine the effect of the compound on cell survival in comparison with vehicle.

The biological results are summarized in Table 1, where each compound was tested at 2 µM and where A represents a value greater than 50%, B represents a value between 10% and 50%, C represents a value between 1% and 10%, and D represents a value no greater than 1%.

TABLE 1

| Cmpd. | Cell Survival |
|---|---|
| A4 | D |
| C1 | A |
| C2 | A |
| C3 | B |
| C4 | B |
| C5 | B |
| C6 | C |
| C7 | C |
| C8 | D |
| C9 | D |
| C10 | D |
| C11 | D |
| C12 | D |
| C13 | D |
| C14 | D |
| C15 | D |
| C16 | D |
| C17 | D |
| C18 | B |
| C19 | A |
| C20 | A |
| C21 | C |
| C22 | D |

Cell Rescue Assays

Protection against Thapsigargin (TG)-induced Cell-death. Human embryonic kidney (HEK293) cells were grown in Dulbecco's Modified Eagle's Medium (DMEM) with 10% FBS and 1% antibiotic antimycotic solution (ABAM). Mouse neuroblastoma (N2a) cells were grown in 1:1 DMEM:OPTI-MEM® with 5% FBS and 1% ABAM. All cells were grown in 10% $CO_2$ in a humidified environment of the incubator. Cells grown in 96-well plates were exposed to a test compound (20 µM) for 2 hrs before addition of thapsigargin (15 µM for HEK293 cells and 1 µM for N2a cells) to induce ER stress. After incubation in cell-culture incubator for 24 hrs, ALAMARBLUE® regent (10% v/v) was added to the wells. Fluorescence reading was taken 2 hrs after the addition of the ALAMARBLUE® regent. Cell-viability was calculated as a percentage of relative fluorescence unit (RFU) compared to control. Vehicle-treated control cells showed similar viability as that of untreated cells.

Protection against Hydrogen Peroxide-induced Cell-death. N2a cells grown in 96-well plates were exposed to a test compound (40 µM) for 2 hrs before addition of hydrogen peroxide (200 µM). After 40 min of incubation with hydrogen peroxide, ALAMARBLUE® regent (10% v/v) was added to the wells. Fluorescence reading was taken 2 hrs after the addition of the ALAMARBLUE® regent. Cell-viability was calculated as a percentage of relative fluorescence unit (RFU) compared to control. Vehicle-treated control cells showed similar viability as that of untreated cells.

The results are summarized in Table 2, where A represents a value greater than 50% cell rescue, B represents a value between 10% to 50% cell rescue, C represents a value between 1% to 10% cell rescue, and D represents a value no greater than 1% cell rescue.

$Ca^{2+}$-ATPase Assay

A $Ca^{2+}$-ATPase assay was performed using microsomal preparations from HEK 293 cells at a series of calcium concentrations corresponding to the physiological range, relative to controls. The ATP hydrolysis rate was measured over a range of calcium concentrations in the presence of test compounds using an NADH-linked, enzyme-coupled ATPase assay adapted for 96-well microplates, with $V_{max}$ determined by fitting the ATPase calcium-dependence to the Hill function. Each well contained 2 µg or 7 g of SR vesicles (optimized for skeletal or cardiac SR, respectively), 50 mMv MOPS (pH 7.0), 100 mMv KCl, 5 MMv MgClz, 1 mMv EGTA, 0.2 mlv NADH, 1 mlv phosphoenol pyruvate, 5 IU pyruvate kinase, 5 IU lactate dehydrogenase, and 3.5 µg/mLh A23187 (a calcium ionophore). $CaCl_z$ was added to set free [$ICa^{21}$] to the specific values. The assay was started upon addition of ATP at a final concentration of 5 m and read in a SpectraMax Plus microplate spectrophotometer. Compounds A12, A13, and C19 increased baseline ATPase activity by 10-15%; and compounds C18 and C20 increased ATPase activity greater than 15%.

TABLE 2

| Cmpd. | HEK293 Cells (TG-induced) | N2a Cells (TG-induced) | N2a Cells ($H_2O_2$-induced) |
|---|---|---|---|
| A8 | A | B | B |
| A9 | A | A | B |
| A12 | A | B | B |
| A27 | | | A |
| B1 | | B | A |
| B2 | | A | B |
| B3 | A | B | B |
| B4 | A | B | B |
| C5 | A | A | B |
| C10 | A | B | B |
| C18 | A | A | B |
| C19 | A | B | A |

TABLE 2-continued

| Cmpd. | HEK293 Cells (TG-induced) | N2a Cells (TG-induced) | N2a Cells ($H_2O_2$-induced) |
|---|---|---|---|
| C20 | B | B | B |
| E1 |   | A |   |
| E2 |   | A |   |
| E3 |   | A |   |
| E4 |   | B |   |
| F1 |   | A |   |
| F2 |   | A |   |
| F3 |   | A |   |
| F4 |   | B |   |
| G1 |   |   | B |
| G2 |   |   | A |
| G3 |   |   | B |
| G4 |   |   | B |
| G5 |   |   | B |
| G6 |   |   | A |
| G7 |   |   | A |
| H1 |   |   | B |
| H2 |   |   | B |
| H3 |   |   | A |
| H4 |   |   | A |
| H5 |   |   | B |
| H6 |   |   | B |
| H7 |   |   | B |
| H8 |   |   | B |
| H9 |   |   | A |
| H10 |   |   | B |
| H11 |   |   | A |

Determination of the Effect of a SERCA Agonist on $[Ca^{2+}]_{ER}$

The effect of a test compound, compound A12, on $[Ca^{2+}]_{ER}$ was assessed in HeLa cells overexpressing BI-1, which mimic the diabetic state and have reduced $[Ca^{2+}]_{ER}$. To directly measure ER $Ca^{2+}$ content, a genetically encoded $Ca^{2+}$ indicator, ER cameleon, was used. HeLa cells were transfected with ER-cameleon encoding plasmid for 2 days before analysis. Cells were treated with a test compound for 24 hrs and imaged in $Ca^{2+}$-free HBSS upon addition of thapsigargin to deplete ER stores. Emission ratio imaging of the ER cameleon was accomplished using a 430/24 excitation filter, 450-nm dichroic mirror, and two emission filters (475/40 for CFP and 535/25 for YFP). The fluorescence ratio of YFP/CFP is a measure of relative ER $Ca^{2+}$ levels. Compound A12 significantly restored $[Ca^{2+}]_{ER}$.

Determination of the Effect of a SERCA Agonist on the Level of Blood Glucose

Figure 3:
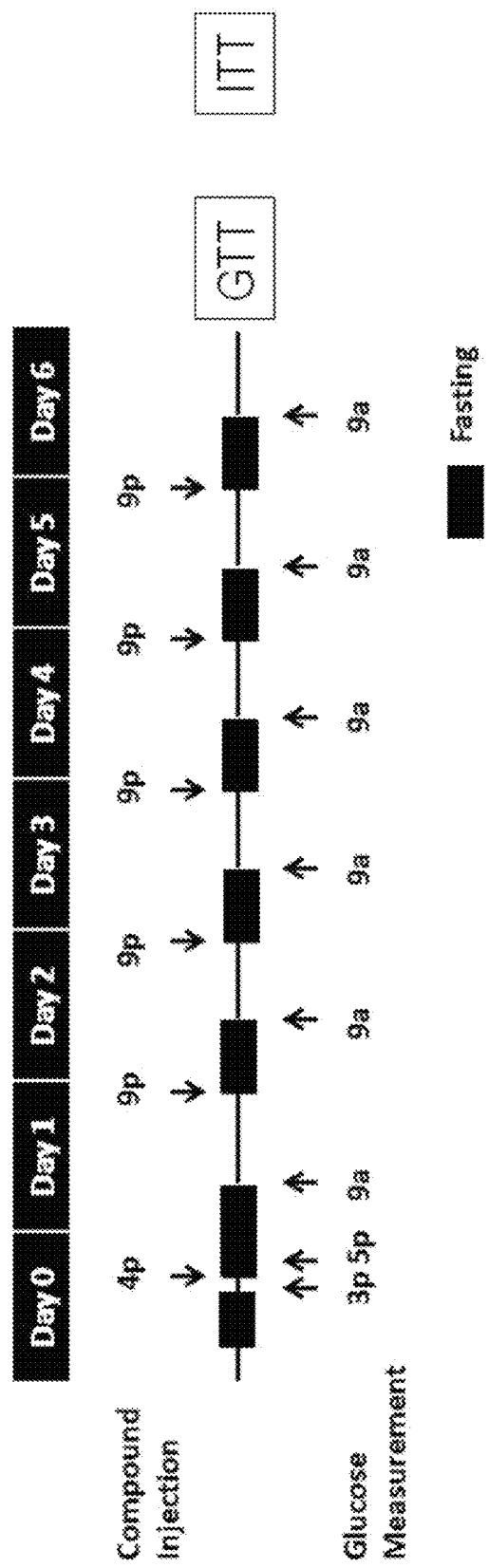
FIG. 3 shows a protocol for assessing the effect of a compound provided herein on diabetic mice.

Ob/ob mice (10 weeks old, n=3) were intraperitoneally (i.p.) injected with 100 μL of a solution containing 0 (vehicle), 10 or 50 mg/kg of a test compound chosen from compounds A12, C18, C19, or C20, once a day for a total of 5 days. The protocol for assessing the effect of the test compound is shown in FIG. 3. Fasting glucose was measured at baseline and 10 hours after the administration of the test compound. Glucose levels were measured in blood samples drawn from the tail vein using the OneTouch Ultra 2 Meter (LifeScan, Inc.). Compounds A12, C18, C19, and C20 significantly lowered blood glucose as early as day 2; and the ob/ob mice maintained a lower glucose level, to a level identical to lean mice, for over a week after the last injection of the test compound.

Determination of the Effect of a SERCA Agonist on the Improvement of Glucose and Insulin Tolerance Both glucose (GTT) and insulin (ITT) tolerance tests were performed following a 10-hr fast and an additional 2-hr after A12 injection with baseline blood glucose measurement taken before the beginning of the test. For the GTT, D-glucose dissolved in 0.9% NaCl was delivered intraperitoneally at a dose of 1 g/kg. The blood glucose level was measured 0, 15, 30, 60, 90, and 120 min after glucose administration. For the ITT, insulin was administered intraperitoneally at a dose of 1 IU/kg. The blood glucose level was measured 0, 15, 30, 60, 90, and 120 min after insulin administration. Glucose levels were measured in blood samples drawn from the tail vein using OneTouch Ultra 2 Meter (LifeScan, Inc.). Glucose tolerance test (GTT) on day 7 post-injection of the ob/ob mice showed that the hyperglycemic response to the i.p. glucose challenge was significantly reduced in compound A12-treated ob/ob mice compared with vehicle; and insulin tolerance test (ITT) on day 10 post-injection showed that insulin-stimulated glucose deposal strongly enhanced in compound A12-treated ob/ob mice compared with vehicle.

Determination of the Effect of a SERCA Agonist on the Improvement of Glucose and Lipid Metabolism The expression of key genes involved in gluconeogenesis and lipogenesis was measured. RNA was isolated from liver samples of the ob/ob mice and mRNA expression of the indicated genes was quantified by Real-time PCR using iTaq Fast SYBR Green Supermix with ROX (Bio-Rad) in a 7500 Real-Time PCR systems (Applied Biosystems) using mouse specific primers. Gene expression is normalized to 18 s. RNA was isolated using Trizol (Invitrogen). cDNA was generated using High Capacity cDNA Reverse Transcription kit (Applied Biosystems). Real-time PCR was performed with iTaq Fast SYBR Green Supermix with ROX (Bio-Rad) in 7500 Real-Time PCR systems (Applied Biosystems) using mouse specific primers. Gene expression was normalized to 18 s. Isolated liver tissue was homogenized in RIPA buffer containing protease inhibitors and phosphatase inhibitors (Roche). Protein samples were matched for their protein concentrations and 30 micrograms of each sample were applied to SDS-PASE and transferred onto nitrocellulose membrane. Membranes were then incubated with the corresponding phosphor or total primary antibodies specific for the desired proteins followed by incubation with appropriate secondary antibodies conjugated to horseradish peroxidase (Pierce) and signal intensities were visualized by Chemiluminescence (Pierce). Films from at least four independent experiments were scanned and densities of the immunoreactive bands were evaluated using NIH Image software. GAPDH (Santa Cruz Biotechnology) was used as a loading control.

Compound A12 significantly reduced the mRNA expression of glucose 6 phosphatase (G6PAse) and phosphoenolpyruvate carboxykinase (PEPCK), known candidates to be involved in glucose homeostasis. Compound A12 also significantly reduced the mRNA expression of a number of lipogenic genes such as stearoyl-CoA desaturase-1 (SCD1), diacylglycerol acyltransferase 2 (DGAT2), fatty acid synthase (FASn), and acetyl co-A and sterol regulatory element binding protein 1c (SREBP1c). Compound A12 increased the expression of the transcription factor peroxisome proliferator-activated receptor α (PPARα) and its target peroxisome proliferator-activated receptor γ coactivated-1 α (PGC1α), known to be involved in lipid oxidation and mitochondrial biogenesis. These data demonstrate that compound A12 influences glucose as well as lipid homeostasis, thus implicating the compound in mediating energy homeostasis in the liver of obese mice.

Protection of Human Pancreatic Islets Under Type 1 Diabetes-Relevant Stress

Human pancreatic islet microtissues treated with cytokines were used to model the conditions of Type 1 Diabetes in vitro. This study tested the effects of compounds on 3-cell viability in human islets under cytokine stress. The model consisted of human islet microtissues from an HLA-A2 positive donor grown and separated in a 96-well plate (1 microtissue per well). The microtissues were treated for 7 days with a cocktail of cytokines (IL1-β 5 ng/mL, IFN-γ 25 ng/mL, TNF-α 25 ng/mL) and compound (5 μM) or vehicle. There were 6 microtissues treated per compound or vehicle. At day 7, the total ATP content was measured using Cell-Titer-Glo (Promega). Compound A17 increased viability over baseline by 10-20%; compounds A12, A13, A19, C19, and C20 increased viability by 20-50%; and compound C18 increased viability by over 50%.

Determination of the Effect of a SERCA Agonist on the Reduction of ER Stress

Protein samples were prepared from livers of ob/ob treated with vehicle (ob) or ob/ob mice treated with 50 mg/kg of the test compound (compound A12). Proteins were analyzed by western blot and quantified. Bands were normalized to GAPDH and expressed as 100% of ob/ob+vehicle (ob). Liver tissues were homogenized with a benchtop homogenizer in an ice-cold tissue lysis buffer. The homogenized samples were centrifuged at 8,000×g for 20 min at 4° C. The lipid layer was removed and the supernatant was transferred into Eppendorf tubes. After centrifuging at 16,000×g for 60 min at 4° C., the supernatants were normalized to the same concentration and boiled at 100° C. in 1× Laemmli buffer for 5 min. The lysate was cooled to room temperature before loading for Western blot analysis. Protein lysate was resolved on SDS polyacrylamide gel and transferred onto PVDF membrane at a voltage of 100 V for 2 hrs at 4° C. The membrane was blocked in 10% blocking reagent and incubated overnight with a primary antibody in Tris-buffered saline solution/Tween (TBST)/10% blocking reagent at 4° C. After incubation, the membrane was washed three times in TBST for 20 min and incubated at room temperature with a secondary antibody in TBST/10% blocking reagent for 1 hr. The membrane was washed three times for 20 min and developed using a chemiluminescence assay system. To strip a membrane for another primary antibody, the membrane was agitated at 50° C. for 20 min in a box with stripping buffer (2% SDS and 100 mM 2-mercaptoethanol in TBS, pH 7.5). The membrane was washed three times for 20 min before blocking and an incubation with a primary antibody.

The administration of the test compound as a SERCA agonist led to improvement in ER function as evidenced by the expression protein markers of ER stress. Compounds A12 and C18 significantly reduced the phosphorylation of PKR-like ER kinase (PERK) and eIF2α. Dephosphorylation of PERK and eIF2α is indicative of alleviation of ER stress response. The test compounds also significantly reduced the expression of the pro-apoptotic transcription factor C/EBP homologous protein (CHOP), suggesting that the test compounds may also be involved in attenuation of ER stress-induced apoptosis.

Activation of SERCA

Test compounds were characterized over a range of concentrations using an NADH-linked, enzyme-coupled ATPase assay. Each well contained 2 mg or 7 mg of SR vesicles (optimized for skeletal or cardiac SR, respectively), 50 mM MOPS (pH 7.0), 100 mM KCl, 5 mM $MgCl_2$, 1 mM EGTA, 0.2 mM NADH, 1 mM phosphoenol pyruvate, 5 IU pyruvate kinase, 5 IU lactate dehydrogenase, and 3.5 mg/mL A23187 (a calcium ionophore), and $CaCl_2$ was added to set free [Ca2+] to the specific values. The assay was started upon addition of ATP at a final concentration of 5 mM, and read in a SpectraMax Plus microplate spectrophotometer and the ATPase activities were fitted using the Hill function.

$EC_{50}$ values were determined as the concentrations of the test compounds that were required for 50% activation of the maximum $V_{max}$.

The biological results are summarized in Table 3, wherein, for $EC_{50}$ values, A represents a value smaller than 20 μM, B represents a value between 20 μM to 100 μM, C represents a value greater than 100 μM; and for increases in $V_{max}$ at 10 μM, A' represents an increase greater than 50%, B' represents an increase between 20 to 50%, and C' represents an increase no greater than 20%.

Selectivity Determination

Compound A12 was tested at 10 μM in duplicate against a panel of 164 commonly tested biological targets in the pharmaceutical and biotech industries. The methods used here for each target were adapted from the scientific literature to maximize reliability and reproducibility. Reference standards were run as an integral part of each assay to ensure the validity of the results obtained. Among the 164 targets, compound A12 showed significant responses only against human adenosine $A_{2A}$, human serotonin (5-hydroxytryptamine) $5-HT_{2B}$, rabbit monoamine transporter, and human nerepinephrine (NET) transporter.

TABLE 3

| Cmpd # | ER Stress $EC_{50}$ | $CSR^1$ $EC_{50}$ | $SSR^2$ $EC_{50}$ | Increase in $V_{max}$ at 10 μM |
|---|---|---|---|---|
| A4 | C | A | | B' |
| A7 | | A | | B' |
| A8 | | | A | C' |
| A10 | | | A | C' |
| A11 | | A | | A' |
| A12 | A | A | A | A' |
| A13 | A | A | A | B' |
| A17 | B | A | A | A' |
| A19 | A | A | A | A' |
| A23 | | A | A | A' |
| A27 | A | | | A' |
| B1 | A | | A | B' |
| B2 | A | | A | A' |
| B3 | | B | | C' |
| C5 | | | A | B' |
| G2 | A | | | A' |
| G6 | A | | | C' |
| G7 | A | | | A' |

[1]CSR: cardiac SR.
[2]SSR: skeletal SR.

Treatment Alzheimer's Disease (AD) and Parkinson's Disease (PD)

Mouse Model: PS1/APP mice (PS1M146V and APPSWE) (Howlett et al., Brain Res. 2004, 1017, 130-136) were used. Age-matched NTg controls were on the same background strain (C57bl6/J9).

Drug Dosing: Compound A12 was administered intraperitoneally (IP, 10 mg/kg in sterile water) to AD--Tg and NonTg mice at (2) daily injections for 4 weeks starting at 5 months for the TASTPM (coinciding with moderate plaque formation and onset of cognitive deficits. Control mice were administered 0.9% saline daily.

Brain Slice Preparation: Mice were deeply anesthetized with halothane and rapidly decapitated. The brains were extracted rapidly and 300 or 400 μm-thick transverse hippocampal slices were cut with a vibrating microtome into ice-cold oxygenated artificial cerebrospinal fluid (aCSF) with the following composition (in mM): 125 NaCl, 2.5 KCl, 1.25 $KH_2PO_4$, 1.2 $MgSO_4$, 2 $CaCl_2$, 10 dextrose, and 25 $NaHCO_3$.

Alzheimer's model behavioral tests: Compound A12 was administered intraperitoneally (IP, 10 mg/kg) to APPSWE/

Figure 6:
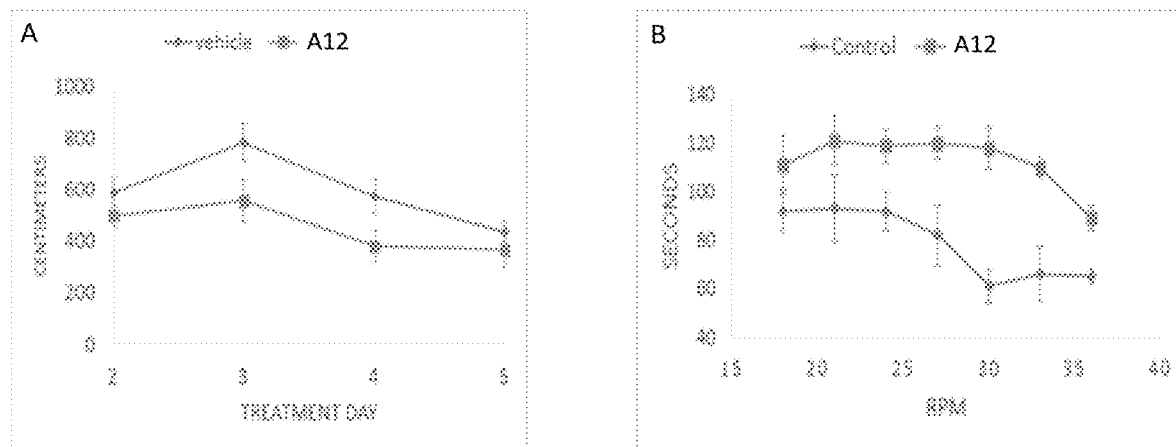
FIG. 6 demonstrates the effects of treatment with compound A12 on memory and coordination by using the Morris water maze (A) and the Rotarod (B) tests, respectively, in the APP-PS1 mouse model of Alzheimer's disease

PSEN1dE9 double-transgenic mice, with daily injections for 4 weeks (5 days every week) starting at 4 months. Mice were tested after the last administration of A12 or vehicle solution according to the dosing schedule. Briefly, the mice were shown a visible platform that was subsequently removed. The distance that the mice swim searching for the platform was measured, with a shorter distance indicating increased memory. As shown in FIG. 6 (A), in the hidden platform test, the A12 treated mice showed a decrease in total distance compared with vehicle treated mice. Motor coordination, strength, and balance was assessed using the Rotarod test (FIG. 6, B). Mice were first trained until they could remain on a rotarod revolving at 16 rpm for three consecutive 120 sec trials. The next day the mice were placed back on the rotarod for a single trial at 18 rpm (maximum duration 120 sec). The duration a mouse could remain on the rotarod was recorded, and the mouse was then returned to its home cage. The speed of the rotarod was then increased to 21 rpm, and all mice were given another test trial. This process was repeated for rotarod speeds of 24, 27, 30, 33, and 36 rpm. All the speeds were repeated twice for the mice in different groups, interval 30 min every time. The Mean values of two tests were analyzed. The mice maintained longer time on the rotarod with more ability of motor coordination, strength and balance.

$Ca^{2+}$ Imaging: $Ca^{2+}$ imaging within individual neurons was performed in brain slice preparations using a custom-made video-rate multiphoton-imaging system based on an upright Olympus BX51 microscope frame. Individual neurons were filled with the $Ca^{2+}$ indicator bis-fura-2 (50 µM) via the patch pipette. Laser excitation was provided by 100 fs pulses at 780 nm (80 MHz) from a Ti:sapphire laser (Mai Tai Broadband, Spectra-Physics). The laser beam was scanned by a resonant galvanometer (General Scanning Lumonics), allowing rapid (7.9 kHz) bidirectional scanning in the x-axis, and by a conventional linear galvanometer in the y-axis, to provide a full-frame scan rate of 30 frames/s. The laser beam was focused onto the tissue through an Olympus 40 x water-immersion objective (numerical aperture 0.8). Emitted fluorescence light was detected by a wide-field photomultiplier (Electron Tubes) to derive a video signal that was captured and analyzed by Video Savant 5.0 software (IO Industries). Further analysis of background-corrected images was performed using MetaMorph software. For clarity, results are expressed as inverse ratios so that increases in $[Ca^{2+}]$ correspond to increasing ratios. The % change is calculated as $[(F/\Delta F)-1]\times 100$, where F is the average resting fluorescence at baseline and $\Delta F$ is the decrease of fluorescence reflecting Ca release. Differences between drug- and saline-treated groups were assessed using two-way ANOVA and Scheffe post hoc analysis for significance ($p<0.05$). For data sets measuring somatic $Ca^{2+}$ responses, the nucleus was excluded.

Aβ Deposition

Mice were transcardially perfused with ice-cold PBS (3 mL) followed by 4% paraformaldehyde (5 mL). Brains were extracted and fixed overnight in 30% sucrose-cryoprotectant solution. Coronal hippocampal sections 40 m thick were cut on a cryostat and collected in TBS (0.1 M Tris, 0.9% saline, pH 7.4).

Thioflavin S Staining: Free-floating hippocampal sections were washed with TBS (4×3 min). The sections were soaked in 0.5% thioflavin S (in 50/50 ethyl alcohol/distilled water, Sigma--Aldrich) for 10 min, followed by 2×3 min washes with 50% ethyl alcohol. Sections were washed again with TBS (2×3 min), mounted with minimal drying, and cover-slipped with anti--fade mounting medium PVA-DABCO for microscopy.

Confocal images of immunolabeled tissue were obtained using 4 X and 10 X objective lenses on the Olympus Fluoview confocal microscope. Density of amyloid plaques was quantified by averaging the percent area staining positive (thresholded above background staining, as determined by software parameters and experimenter confirmation) within the hippocampus and cortex from 3-5 sections from each experimental animal using MetaMorph Software (Molecular Devices). There were no significant differences in the intensity of background threshold values across animal strains or treatment conditions ($p>0.05$). The experimenter was blind to animal strain and treatment condition.

In vivo treatment with compound A12 restores ER $Ca^{2+}$ signaling in AD mice. A). Pseudocolored 2-photon images depict Ca2+ responses to caffeine (10 mM, 60 sec) for saline-treated PS1/APP (Figure below, left) and compound A12 treated PS1/APP (middle) CA1 pyramidal neurons. Image on right is caffeine response from a NonTg control neuron. B). Bar graph of peak $Ca^{2+}$ responses from (A) shows normalized RyR-Ca2+ response in compound A12-treated PS1/APP (red) compared to saline-treated PS1/APP (black) and NonTg-saline treated neurons.

Figure 4:
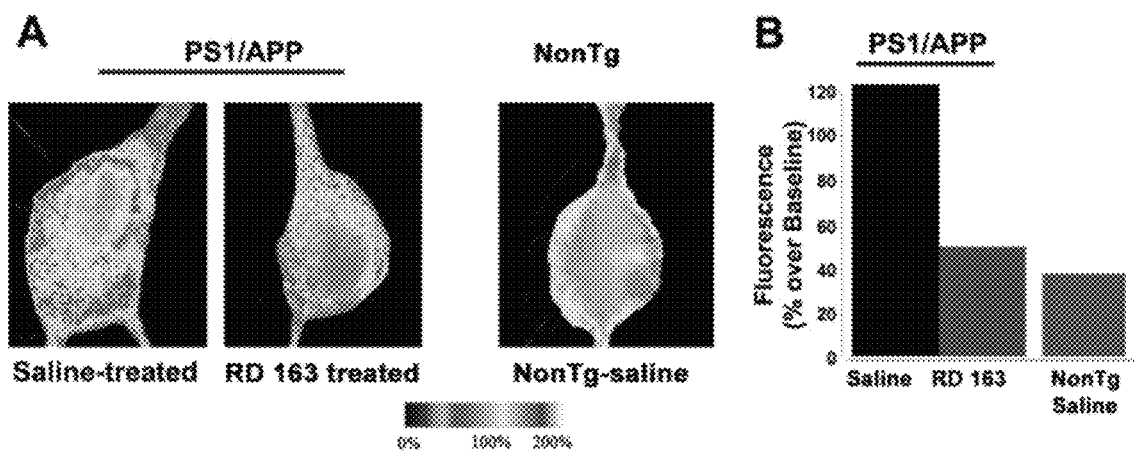
FIG. 4 shows (A) pseudocolored 2-photon images depicting $Ca^{2+}$ responses to caffeine (10 mM, 60 sec) for the CA1 pyramidal neurons of saline-treated PS1/APP mice, compound A12 (RD 163) treated PS1/APP mice, and Non-Tg-saline treated mice; and (B) normalized RyR-$Ca^{2+}$ responses for the CA1 pyramidal neurons of saline-treated PS1/APP mice, compound A12 treated PS1/APP mice, and Non-Tg-saline treated mice.
Figure 5:
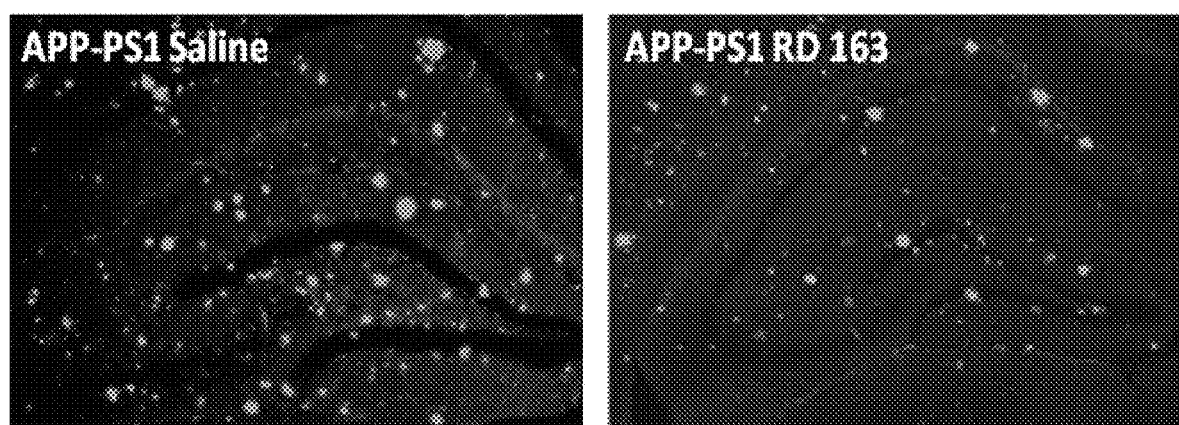
FIG. 5 shows the effect of compound A12 on the amyloid plaques formation in APP-PS1 mice.

Results are shown in FIGS. 4 and 5. FIGS. 4 show that in vivo treatment with compound A12 (RD 163) restores ER $Ca^{2+}$ signaling in AD mice. FIG. 5 shows that amyloid plaques stained with Thioflavin S are reduced in APP-PS1 mice treated with compound A12 (RD 163) for 4 weeks (10 mg/kg, ip) compared to saline treated APP-PS1 mice. Mice were ~6 months of age.

Figure 7:
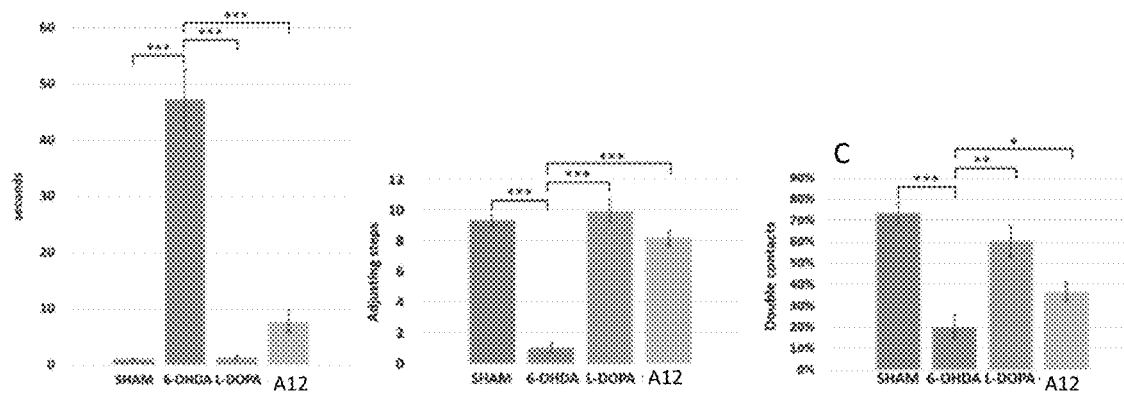
FIG. 7 shows the effect of treatment of A12 on dyskinesia in 6-OHDA-lesioned rats. The data show the initiation time test (A), the stepping test (B), and the cylinder test (C).

Behavioral tests in the 6-hydroxydopamine (6-OHDA)-lesioned rat model of Parkinson's disease. Male Wistar rats were trained for both the stepping and initiation time (IT) tests 6 days before treatment with 6-OHDA or NaCl (day −6). 5 days before treatment with 6-OHDA, animals from groups 1 to 3 were given vehicles [NaCl or a mixture of DMSO (10%)/tween 80 (10%)/water (80%)] once daily for 16 days. Animals from group 4 were administered once daily with A12 (10 mg/kg). All the treatments were given via the IP route, once daily, Sunday excluded. Surgery was performed on D0 under ketamine (50 mg/kg) and xylazine (10 mg/kg). Animals received a unilateral injection of 6-OHDA, 6 l (sigma Aldrich) in the left substantia nigra pars compacta. During surgery, local analgesia was achieved using subcutaneous injections of lidocaine. At the end of surgery, animals were treated with buprenorphine (0.05 mg/kg, S.C.). On D11, animals were given L-DOPA+ benserazide or A12 before akinesia tests were performed. For the IT test, only one of the two forelimbs was left free to move and the time that is necessary to initiate the movement toward the plane surface was recorded, using 180 sec as break-off point. As can be seen in FIG. 7 (A), the animals lesioned with 6-OHDA had an increase in initiation time that was reduced by A12. In the stepping test, the rat was held by the experimenter and only one of the two forelimbs was left free to move above a plane surface. The other hand fixed the forelimb not to be monitored with one paw touching the table. The animal was then be moved slowly forward by the experimenter. The number of adjusting steps was counted for the right paw. FIG. 7 (B) shows the results of the stepping test with L-DOPA and A12. The lesioned animals had a drastic reduction in the number of adjusting steps that was increased by A12. In the cylinder test, animals were placed in a Plexiglas cylinder and, immediately, videotaped for 15 min. During this time, the numbers of contacts made on the cylinder wall with both the ipsilateral, the contralateral, and the two paws simultaneously (double contacts) were recorded and then expressed as a percentage of the total number of contacts. FIG. 7 (C) details the results of treatment of A12 in the cylinder test. The 6-OHDA animals show a reduced number of contacts that is increased by A12.

Pharmacokinetics in Sprague Dawley Rats

Pharmacokinetics of a test compound, compound A12, was assessed in Sprague Dawley rats. The compound was formulated at 1 mg/mL in DMSO/Tween 80/water (10/10/80, vol/vol/vol) and dosed at 1 mg/kg intravenous (i.v.) or 2 mg/kg by oral gavage (P.O.) in triplicate. Blood was drawn at 5 min, 15 min, 30 min, 1 hr, 2 hrs, 4 hrs, 6 hrs, and 8 hrs into EDTA containing tubes and plasma was harvested by centrifugation. Plasma (25 µL) was treated with acetonitrile (125 µL) containing an internal standard. The sample was then centrifuged for 5 min at 4,000 rpm in a tabletop centrifuge and the filtrate was collected. The filtrate was injected onto a Thermo Betasil C18 HPLC column 5 (50×2.1 mm). Mobile Phase A was water with 0.1% formic acid. Mobile Phase B was acetonitrile with 0.1% formic acid. Separation was achieved using a gradient of 90% A/10% B to 5% A/95% B over 7 min. An API Sciex 4000 equipped with a turbo ion spray source was used for all analytical measurements. A positive ion MRM method was developed. Peak areas of the product ion were measured against the peak areas of the internal standard. Data was fit using WinNonLin (Pharsight Corporation, Mountain View, Calif.). Oral pharmacokinetic properties of compound A12 are: $T_{1/2}$: 1.17 hr; $C_{max}$: 0.26 µM; $AUC_{last}$ 0.41 µM·hr; $CL_{obs}$: 251 mL/min/kg; and F %: 13.22.

Brain barrier penetration of compound A12 was also determined similarly at a dose 10 mg/kg IP in mice. The brains of the mice were harvested 1 hr after dosing. The brain/plasma ratio was 2.6.

Pharmacokinetics of compounds A13, A17, and A19 were assessed in Sprague Dawley rats. Compound A13 was formulated in 0.2% DMA/0.5% SOLUTOL®/99.3% saline. Compounds A17 and A18 were formulated in 0.2% DMA/2% SOLUTOL®/97.8% saline. The results are summarized in Table 4.

Pharmacokinetics of compound A13 was assessed in dogs. Compound A13 was formulated in 0.2% DMA/0.5% SOLUTOL®/99.3% saline. The results are summarized in Table 5. For pharmacokinetic evaluation, 3 male Beagle dogs were intravenously (IV) dosed (1 mg/kg body weight) and 3 male Beagle dogs were orally (PO) dosed (10 mg/kg body weight) with a test compound. Blood (approximately 1.0 mL) was collected via femoral vein into tubes containing $K_3$EDTA anticoagulant at 0, 0.017, 0.083, 0.5, 1, 2, 4, 6, 8, and 24 hours post-dosing. Plasma samples were analyzed by LC-MS/MS. The analytical results were confirmed using quality control samples for intra-assay variation. The accuracy of >66% of the quality control samples was between 80-120% of the known value(s). A standard set of pharmacokinetic parameters were generated from concentration data including Area Under the Curve ($AUC_{0-t}$ and $AUC_{0-inf}$), elimination half-lives, clearances, volume of distribution and bioavailabilities (based on AUC0-t), maximum plasma concentration ($C_0$; $C_{max}$), and time to reach maximum plasma concentration ($T_{max}$).

TAABLE 4

| Compd. | Dosing | $AUC_{0-t}$ (µg/L · hr) | $AUC_{0-\infty}$ (µg/L · hr) | $MRT_{0-\infty}$ (hr) | $t_{1/2}$ (hr) | $T_{max}$ (hr) | Vz (L/kg) | CL (L/hr/kg) | $C_{max}$ (nmol/mL) | F (%) |
|---|---|---|---|---|---|---|---|---|---|---|
| A13 | IV (2 mg/kg) | 842 ± 31 | 847 ± 29 | 0.45 ± 0.05 | 2.01 ± 0.46 | 0.08 ± 0.00 | 6.87± 1.73 | 2.36 ± 0.08 | 8.37 ± 1.10 | 5.5 |
|  | PO (10 mg/kg) | 232 ± 154 | 234 ± 154 | 0.64 ± 0.23 | 0.38 ± 0.18 | 0.42 ± 0.14 |  |  | 0.80 ± 0.35 |  |
| A17 | IV (2 mg/kg) | 380 ± 66 | 381 ± 66 | 0.59 ± 0.08 | 0.90 ± 0.14 | 0.02 ± 0.00 | 7.01 ± 2.02 | 5.34 ± 0.85 | 4.42 ± 0.64 | 31 |
|  | PO (10 mg/kg) | 583 ± 119 | 587 ± 120 | 1.13 ± 0.06 | 1.14 ± 0.57 | 0.25 ± 0.00 |  |  | 1.69 ± 0.74 |  |
| A19 | IV (2 mg/kg) | 299 ± 17 | 309 ± 17 | 0.46 ± 0.04 | 0.45 ± 0.03 | 0.02 ± 0.00 | 0.00 ± 0.00 | 0.01 ± 0.00 | 3.85 ± 0.46 | 25 |
|  | PO (10 mg/kg) | 375 ± 105 | 385 ± 99 | 0.75 ± 0.10 | 0.44 ± 0.08 | 0.33 ± 0.14 |  |  | 1.25 ± 0.40 |  |

TABLE 5

| Compd. | Dosing | $AUC_{0-t}$ (µg/L · hr) | $AUC_{-\infty}$ (µg/L · hr) | $MRT_{0-\infty}$ (hr) | $t_{1/2}$ (hr) | $T_{max}$ (hr) | Vz (L/kg) | CL (L/hr/kg) | $C_{max}$ (nmol/mL) | F (%) |
|---|---|---|---|---|---|---|---|---|---|---|
| A13 | IV (1 mg/kg) | 95 ± 12 | 96 ± 12 | 0.21 ± 0.06 | 0.34 ± 0.14 | 0.02 ± 0.00 | 5.4 ± 2.6 | 10.6 ± 1.4 | 2.2 ± 0.5 | 1.4 |
|  | PO (10 mg/kg) | 13 ± 6 | 7 | 0.62 | 0.37 | 0.36 ± 0.24 |  |  | 0.08 ± 0.06 |  |

Pharmacokinetics in CD-1 Mice

Pharmacokinetics of test compounds were assessed in CD-1 mice. The compounds were formulated at 1 mg/mL in DMSO/Tween 80/water (10/10/80, vol/vol/vol) and dosed at 2 mg/kg intravenous (i.v.) or 10 mg/kg by oral gavage (P.O.) in triplicate. Blood was drawn at 0.25 h, 0.5 h, 1 hr, 2 hrs, 4 hrs, 8 hrs, and 24 hrs into EDTA containing tubes and plasma was harvested by centrifugation. Plasma (10 µL) containing 50% acetonitrile in water (5 µL) was added to 200 µL of ACN containing an internal standard. The samples were vortexed for 30 s. After centrifugation at 4° C. and 4,000 rpm for 15 min, the supernatant was diluted 3 times with water. Then, 20 µL of diluted supernatant was injected into the LC/MS/MS system for quantitative analysis. The samples were injected onto an Agilent ZORBAX XDB-Phenyl 5 column (50×2.10 mm). Mobile Phase A was water with 0.1% formic acid. Mobile Phase B was acetonitrile with 0.1% formic acid. Separation was achieved using a gradient of 70% A/30% B to 0% A/100% B over 2.10 min. A Shimadzu LCMS-8050 equipped with a turbo ion spray source was used for all analytical measurements. A positive ion MRM method was developed. Peak areas of the product ion were measured against the peak areas of the internal standard. Data was fit using WinNonLin (Pharsight Corporation, Mountain View, Calif.). The results are shown in Table 6.

TABLE 6

| Cmpd | Structure | $C_{max}$ (µM) | $t_{1/2}$ (h) | AUC (ng·h/ml) | F (%) |
|---|---|---|---|---|---|
| A12 | 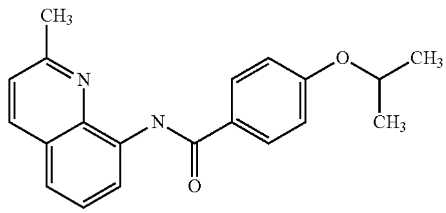 [SMILES: Cc1ccc2cccc(NC(=O)c3ccc(OC(C)C)cc3)c2n1] | 0.2 | 0.223 | 25.1 | 2.3 |
| A13 | 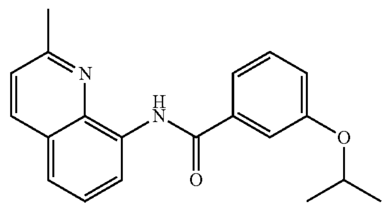 [SMILES: Cc1ccc2cccc(NC(=O)c3cccc(OC(C)C)c3)c2n1] | 0.12 | 0.84 | 26 | 3.1 |
| B1 | 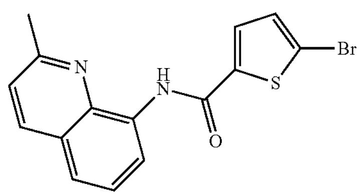 [SMILES: Cc1ccc2cccc(NC(=O)c3ccc(Br)s3)c2n1] | 0.08 | 0.7 | 21 | 2.9 |
| C18 | 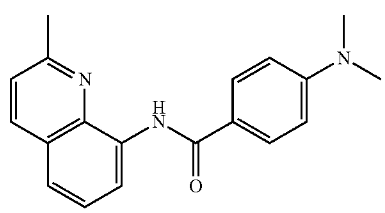 [SMILES: Cc1ccc2cccc(NC(=O)c3ccc(N(C)C)cc3)c2n1] | 0.9 | 0.89 | 380 | 35 |
| C19 | 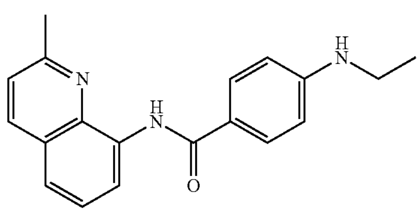 [SMILES: CCNc1ccc(C(=O)Nc2cccc3ccc(C)nc23)cc1] | 0.85 | 2.3 | 344 | 27 |
| C20 | 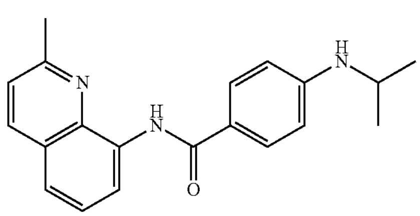 [SMILES: Cc1ccc2cccc(NC(=O)c3ccc(NC(C)C)cc3)c2n1] | 0.86 | 0.66 | 330 | 28 |

TABLE 6-continued

| Cmpd | Structure | $C_{max}$ (µM) | $t_{1/2}$ (h) | AUC (ng·h/ml) | F (%) |
|---|---|---|---|---|---|
| G2 | 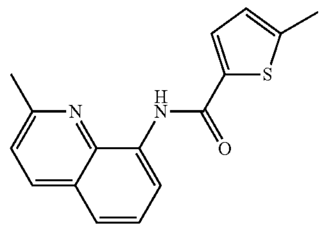 [SMILES: Cc1ccc2cccc(NC(=O)c3ccc(C)s3)c2n1] | 0.02 | 0.56 | 4.5 | 0.85 |
| G8 | 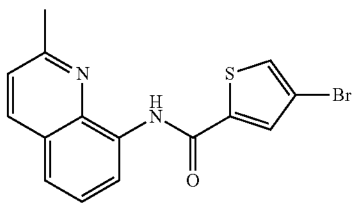 [SMILES: Cc1ccc2cccc(NC(=O)c3cc(Br)cs3)c2n1] | 0.01 | 0.6 | 0.78 | 0.12 |

Compound Synthesis

3-Methyl-N-(2-methylquinolin-8-yl)butanamide A1

3-Methylbutanoyl chloride (120 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A1. ESI-MS: m/z 243 [M+H]+.

N-(2-Methylquinolin-8-yl)pivalamide A2

2,2-Dimethylpropanoyl chloride (120 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A2. ESI-MS: m/z 243 [M+H]+.

3,3-Dimethyl-N-(2-methylquinolin-8-yl)butanamide A3

3,3-Dimethylbutyryl chloride (134 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A3. ESI-MS: m/z 257 [M+H]+.

4-(tert-Butyl)-N-(2-methylquinolin-8-yl)benzamide A4

4-tert-Butylbenzoyl chloride (197 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A4. ESI-MS: m/z 319 [M+H]+.

4-Butyl-N-(2-methylquinolin-8-yl)benzamide A5

4-Butylbenzoyl chloride (197 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A5. ESI-MS: m/z 319 [M+H]+.

4-Fluoro-N-(quinolin-8-yl)benzamide A6

4-Fluorobenzoyl chloride (158 mg, 1.0 mmol) was dissolved in dichloromethane (2 mL) and cooled to 0° C. This solution was added dropwise to a cooled (0° C.) solution of 8-aminoquinoline (144 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A6. ESI-MS: m/z 267 [M+H]$^+$.

3-Fluoro-N-(quinolin-8-yl)benzamide A7

3-Fluorobenzoyl chloride (158 mg, 1.0 mmol) was dissolved in dichloromethane (2 mL) and cooled to 0° C. This solution was added dropwise to a cooled (0° C.) solution of 8-Aminoquinoline (144 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A7. ESI-MS: m/z 267 [M+H]$^+$.

4-Methoxy-N-(2-methylquinolin-8-yl)benzamide A8

4-Methoxybenzoyl chloride (171 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A8. ESI-MS: m/z 293 [M+H]$^+$.

2-Methoxy-N-(2-methylquinolin-8-yl)benzamide A9

2-Methoxybenzoyl chloride (171 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A9. ESI-MS: m/z 293 [M+H]$^+$.

2-Ethoxy-N-(2-methylquinolin-8-yl)benzamide A10

2-Ethoxybenzoyl chloride (185 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A10. ESI-MS: m/z 307 [M+H]$^+$.

4-Isopropoxy-N-(quinolin-8-yl)benzamide A11

4-Isopropoxybenzoic acid (180 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 µL, 1.5 mmol) was added and the solution was stirred for 10 minutes. To this solution was added 8-aminoquinoline (144 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound A11. ESI-MS: m/z 307 [M+H]$^+$.

4-Isopropoxy-N-(2-methylquinolin-8-yl)benzamide A12

4-Isopropoxybenzoic acid (180 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 µL, 1.5 mmol) was added and the solution was stirred for 10 minutes. To this solution was added 8-aminoquinaldine (158 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound A12. ESI-MS: m/z 321 [M+H]$^+$.

3-Isopropoxy-N-(2-methylquinolin-8-yl)benzamide A13

3-Isopropoxybenzoic acid (180 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 µL, 1.5 mmol) was added and the solution was stirred for 10 minutes. To this solution was added 8-aminoquinaldine (158 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound A13. ESI-MS: m/z 321 [M+H]$^+$.

2-((5-Methoxyquinolin-8-yl)carbamoyl)benzoic acid A14

Phthalic anhydride (148 mg, 1.0 mmol) was dissolved in dichloromethane (2 mL) and cooled to 0° C. This solution was added dropwise to a cooled (0° C.) solution of 5-methoxyquinolin-8-amine (174 mg, 1.0 mmol) and N,N-diisopropylethylamine (260 µL, 1.5 mmol) in dichloromethane (5 mL). After addition was complete, the mixture was allowed to warm to room temperature and stirred for 20 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A14. ESI-MS: m/z 323 [M+H]$^+$.

2,6-Difluoro-N-(2-methylquinolin-8-yl)benzamide A15

2,6-Difluorobenzoyl chloride (177 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A15. ESI-MS: m/z 299 [M+H]$^+$.

4-Cyano-2-fluoro-N-(2-methylquinolin-8-yl)benzamide A16

4-Cyano-2-fluorobenzoic acid (165 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 µL, 1.5 mmol) was added and the solution was stirred for 10 min. To this solution was added 8-aminoquinaldine (158 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound A16. ESI-MS: m/z 306 [M+H]$^+$.

2-Chloro-4-methyl-N-(2-methylquinolin-8-yl)benzamide A17

2-Chloro-4-methylbenzoic acid (171 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 µL, 1.5 mmol) was added and the solution was stirred for 10 minutes. To this solution was added 8-aminoquinaldine (158 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound A17. ESI-MS: m/z 311 [M+H]$^+$.

3-Chloro-4-methoxy-N-(2-methylquinolin-8-yl)benzamide A18

3-Chloro-4-methoxybenzolic acid (187 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 µL, 1.5 mmol) was added and the solution was stirred for 10 min. To this solution was added 8-aminoquinaldine (158 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound A18. ESI-MS: m/z 327 [M+H]$^+$.

2-Methoxy-3-methyl-N-(2-methylquinolin-8-yl)benzamide A19

2-Methoxy-3-methylbenzoic acid (166 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 µL, 1.5 mmol) was added and the solution was stirred for 10 min. To this solution was added 8-aminoquinaldine (158 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound A19. ESI-MS: m/z 307 [M+H]$^+$.

2,3,4-Trifluoro-N-(2-methylquinolin-8-yl)benzamide A20

2,3,4-Trifluorobenzoyl chloride (195 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A20. ESI-MS: m/z 317 [M+H]$^+$.

N-(Quinolin-8-yl)-1-naphthamide A21

1-Naphthoyl chloride (191 mg, 1.0 mmol) was dissolved in dichloromethane (2 mL) and cooled to 0° C. This solution was added dropwise to a cooled (0° C.) solution of 8-aminoquinoline (144 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A21. ESI-MS: m/z 299 [M+H]$^+$.

2-(4-Chlorophenyl)-N-(2-methylquinolin-8-yl)acetamide A22

4-Chlorophenylacetyl chloride (189 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A22. ESI-MS: m/z 311 [M+H]$^+$.

3-(4-Methoxyphenyl)-N-(2-methylquinolin-8-yl) propanamide A23

3-(4-Methoxyphenyl)propionyl chloride (199 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A23. ESI-MS: m/z 321 [M+H]$^+$.

5-(4-Methoxyphenyl)-N-(2-methylquinolin-8-yl) isoxazole-3-carboxamide A24

5-(4-Methoxyphenyl)isoxazole-3-carboxylic acid (219 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 μL, 1.5 mmol) was added and the solution was stirred for 10 minutes. To this solution was added 8-aminoquinaldine (158 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound A24. ESI-MS: m/z 360 [M+H]$^+$.

6-Chloro-N-(2-methylquinolin-8-yl)nicotinamide A25

6-Chloronicotinoyl chloride (176 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A25. ESI-MS: m/z 298 [M+H]$^+$.

3-Chloro-N-(2-methylquinolin-8-yl)benzo[b]thiophene-2-carboxamide A26

3-Chlorobenzothiophene-2-carbonyl chloride (231 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A26. ESI-MS: m/z 353 [M+H]$^+$.

N-(2-Methylquinolin-8-yl)benzofuran-2-carboxamide A27

Method 1. Benzofuran-2-carbonyl chloride (181 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A27. ESI-MS: m/z 303 [M+H]$^+$.

Method 2. Benzofuran-2-carboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution, 8-aminoquinaldine (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product A27. ESI-MS: m/z 303 [M+H]$^+$.

2-(Quinolin-8-yl)-2,3-dihydrophthalazine-1,4-dione A28

Phthalic anhydride (148 mg, 1.0 mmol) was dissolved in acetic acid (5 mL). To this solution was added quinolin-8-yl-hydrazine (159 mg, 1.0 mmol) and the solution was heated to 80° C. After heating with stirring for 8 hrs, the mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A28. ESI-MS: m/z 290 [M+H]$^+$.

2-(Quinolin-8-yl)isoindoline-1,3-dione A29

Phthalic anhydride (148 mg, 1.0 mmol) was dissolved in acetic acid (5 mL). To this solution was added 8-aminoquinoline (144 mg, 1.0 mmol) and the solution was heated to 110° C. After heating with stirring for 20 hrs, the mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound A29. ESI-MS: m/z 275 [M+H]+.

5-Bromo-N-(2-methylquinolin-8-yl)thiophene-2-carboxamide B1

Method 1. 5-Bromo-2-thiophenecarbonyl chloride (1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound B1. ESI-MS: m/z 348 [M+H]+.

Method 2. 5-Bromo-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution, 8-aminoquinaldine (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product B1. ESI-MS: m/z 348 [M+H]+.

N-(2-Methylquinolin-8-yl)benzo[b]thiophene-2-carboxamide B2

Method 1. Benzo[b]thiophene-2-carbonyl chloride (196 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound B2. ESI-MS: m/z 319 [M+H]+.

Method 2. 1-Benzothiophene-2-carboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution, 8-aminoquinaldine (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product B2. ESI-MS: m/z 319 [M+H]+.

3-Cyano-N-(quinolin-8-yl)benzamide B3

3-Cyanobenzoyl chloride (1.0 mmol) was dissolved in dichloromethane (2 mL) and cooled to 0° C. This solution was added dropwise to a cooled (0° C.) solution of 8-aminoquinoline (144 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound B3. ESI-MS: m/z 274 [M+H]+.

4-Cyano-N-(2-methylquinolin-8-yl)benzamide B4

4-Cyanobenzoyl chloride (1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound B4. ESI-MS: m/z 288 [M+H]+.

4-Bromo-N-(2-methylquinolin-8-yl)benzamide C1

4-Bromobenzoyl chloride (219 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C1. ESI-MS: m/z 342 [M+H]+.

2-Fluoro-N-(2-methylquinolin-8-yl)benzamide C2

2-Fluorobenzoyl chloride (159 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C2. ESI-MS: m/z 281 [M+H]+.

2-Nitro-N-(2-methylquinolin-8-yl)benzamide C3

2-Nitrobenzoyl chloride (186 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C3. ESI-MS: m/z 308 [M+H]$^+$.

3-Trifluoromethoxy-N-(2-methylquinolin-8-yl)benzamide C4

3-Trifluoromethoxybenzoyl chloride (225 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C4. ESI-MS: m/z 347 [M+H]$^+$.

2-Trifluoromethyl-N-(2-methylquinolin-8-yl)benzamide C5

2-Trifluoromethylbenzoyl chloride (209 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C5. ESI-MS: m/z 331 [M+H]$^+$.

3-Fluoro-N-(2-methylquinolin-8-yl)benzamide C6

3-Fluorobenzoyl chloride (159 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C6. ESI-MS: m/z 281 [M+H]$^+$.

3-Nitro-N-(2-methylquinolin-8-yl)benzamide C7

3-Nitrobenzoyl chloride (186 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C7. ESI-MS: m/z 308 [M+H]$^+$.

4-Nitro-N-(2-methylquinolin-8-yl)benzamide C8

4-Nitrobenzoyl chloride (186 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C8. ESI-MS: m/z 308 [M+H]$^+$.

2-Chloro-N-(2-methylquinolin-8-yl)benzamide C9

2-Chlorobenzoyl chloride (175 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C9. ESI-MS: m/z 297 [M+H]$^+$.

4-Trifluoromethyl-N-(2-methylquinolin-8-yl)benzamide C10

4-Trifluoromethylbenzoyl chloride (209 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C10. ESI-MS: m/z 331 [M+H]+.

4-Trifluoromethoxy-N-(2-methylquinolin-8-yl)benzamide C11

4-Trifluoromethoxybenzoyl chloride (225 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C11. ESI-MS: m/z 347 [M+H]$^+$.

3-Trifluoromethyl-N-(2-methylquinolin-8-yl)benzamide C12

3-Trifluoromethylbenzoyl chloride (209 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C12. ESI-MS: m/z 331 [M+H]$^+$.

4-Ethoxy-N-(2-methylquinolin-8-yl)benzamide C13

4-Ethoxybenzoyl chloride (185 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C13. ESI-MS: m/z 307 [M+H]$^+$.

4-Fluoro-N-(2-methylquinolin-8-yl)benzamide C14

4-Fluorobenzoyl chloride (159 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C14. ESI-MS: m/z 281 [M+H]$^+$.

3-Chloro-N-(2-methylquinolin-8-yl)benzamide C15

3-Chlorobenzoyl chloride (175 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C15. ESI-MS: m/z 297 [M+H]$^+$.

3-Bromo-N-(2-methylquinolin-8-yl)benzamide C16

3-Bromobenzoyl chloride (219 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C16. ESI-MS: m/z 342 [M+H]$^+$.

4-Chloro-N-(2-methylquinolin-8-yl)benzamide C17

4-Chlorobenzoyl chloride (175 mg, 1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C17. ESI-MS: m/z 297 [M+H]$^+$.

4-N,N-Dimethylamino-N-(2-methylquinolin-8-yl)benzamide C18

N,N-Dimethylaminobenzoyl chloride (1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected, and the solvent was removed by rotary evaporation. The residue was purified by preparative reverse-phase HPLC using a water-acetonitrile gradient to afford compound C18. ESI-MS: m/z 306 [M+H]$^+$.

4-(Ethylamino)-N-(2-methylquinolin-8-yl)benzamide C19

4-(Ethylamino)benzoyl chloride (1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 µL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected, and the solvent was removed by rotary evaporation. The residue was purified by preparative reverse-phase HPLC using a water-acetonitrile gradient to afford compound C19. ESI-MS: m/z 306 [M+H]$^+$.

4-(Isopropylamino)-N-(2-methylquinolin-8-yl)benzamide C20

4-(Isopropylamino)benzoyl chloride (1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C20. ESI-MS: m/z 320 [M+H]$^+$.

4-(Isopropylthio)-N-(2-methylquinolin-8-yl)benzamide C21

4-(Isopropylthio)benzoyl chloride (1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C21. ESI-MS: m/z 337 [M+H]$^+$.

4-(Ethylthio)-N-(2-methylquinolin-8-yl)benzamide C22

4-(Ethylthio)benzoyl chloride (1.0 mmol) was dissolved in dichloromethane (2 mL) and cooled to 0° C. This solution was added dropwise to a cooled (0° C.) solution of 8-aminoquinaldine (158 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound C22. ESI-MS: m/z 323 [M+H]$^+$.

8-(4-Isopropoxybenzamido)quinoline-2-carboxylic acid E1

4-Isopropoxybenzoic acid (180 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 μL, 1.5 mmol) was added and the solution was stirred for 10 min. To this solution was added 8-aminoquinoline-2-carboxylic acid (188 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound E1. ESI-MS: m/z 351 [M+H]$^+$.

8-(3-Isopropoxybenzamido)quinoline-2-carboxylic acid E2

3-Isopropoxybenzoic acid (180 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 μL, 1.5 mmol) was added and the solution was stirred for 10 min. To this solution was added 8-aminoquinoline-2-carboxylic acid (188 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound E2. ESI-MS: m/z 351 [M+H]$^+$.

8-(5-Bromothiophene-2-carboxamido)quinoline-2-carboxylic acid E3

5-Bromo-2-thiophenecarbonyl chloride (1.0 mmol) was dissolved in dichloromethane (2 mL) and cooled to 0° C. This solution was added dropwise to a cooled (0° C.) solution of 8-aminoquinoline-2-carboxylic acid (188 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound E3. ESI-MS: m/z 378 [M+H]$^+$.

8-(Benzo[b]thiophene-2-carboxamido)quinoline-2-carboxylic acid E4

Benzo[b]thiophene-2-carbonyl chloride (196 mg, 1.0 mmol) was dissolved in dichloromethane (2 mL) and cooled to 0° C. This solution was added dropwise to a cooled (0° C.) solution of 8-aminoquinoline-2-carboxylic acid (188 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound E4. ESI-MS: m/z 349 [M+H]$^+$.

N-(2-(3,5-Dimethyl-1H-pyrazol-1-yl)quinolin-8-yl)-3-isopropoxybenzamide F1

3-Isopropoxybenzoic acid (180 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 μL, 1.5 mmol) was added and the solution was stirred for 10 min. To this solution was added 2-(3,5-dimethyl-1H-pyrazol-1-yl)quinolin-8-amine (238 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound F1. ESI-MS: m/z 401 [M+H]+.

N-(2-(3,5-Dimethyl-1H-pyrazol-1-yl)quinolin-8-yl)-4-isopropoxybenzamide F2

4-Isopropoxybenzoic acid (180 mg, 1.0 mmol) and N-(3-dimethylaminopropyl)-N'-ethylcarbodiimide hydrochloride (230 mg, 1.2 mmol) were dissolved in dimethylformamide (5 mL). N,N-Diisopropylethylamine (260 μL, 1.5 mmol) was added and the solution was stirred for 10 min. To this solution was added 2-(3,5-dimethyl-1H-pyrazol-1-yl)quinolin-8-amine (238 mg, 1.0 mmol) and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford compound F2. ESI-MS: m/z 401 [M+H]+.

5-Bromo-N-(2-(3,5-dimethyl-1H-pyrazol-1-yl)quinolin-8-yl)thiophene-2-carboxamide F3

5-Bromo-2-thiophenecarbonyl chloride (1.0 mmol) was dissolved in dichloromethane (2 mL) and cooled to 0° C. This solution was added dropwise to a cooled (0° C.) solution of 2-(3,5-dimethyl-1H-pyrazol-1-yl)quinolin-8-amine (238 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound F3. ESI-MS: m/z 428 [M+H]+.

N-(2-(3,5-Dimethyl-1H-pyrazol-1-yl)quinolin-8-yl)benzo[b]thiophene-2-carboxamide F4

Benzo[b]thiophene-2-carbonyl chloride (196 mg, 1.0 mmol) was dissolved in dichloromethane (2 mL) and cooled to 0° C. This solution is added dropwise to a cooled (0° C.) solution of 2-(3,5-dimethyl-1H-pyrazol-1-yl)quinolin-8-amine (238 mg, 1.0 mmol) and N,N-diisopropylethylamine (260 μL, 1.5 mmol) in dichloromethane (5 mL). After addition was complete, the mixture was allowed to warm to room temperature and stirred for 2.5 hrs. The mixture was diluted with water and extracted with 2 volumes of dichloromethane. The organic layers were collected and the solvent was removed by rotary evaporation. The residue was purified by preparative reverse-phase HPLC using a water-acetonitrile gradient to afford compound F4. ESI-MS: m/z 399 [M+H]+.

N-(2-Methylquinolin-8-yl)thiophene-2-carboxamide G1

2-Thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution, 8-aminoquinaldine (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product G1. ESI-MS: m/z 269 [M+H]+.

5-Methyl-N-(2-methylquinolin-8-yl)thiophene-2-carboxamide G2

5-Methyl-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinaldine (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product G2. ESI-MS: m/z 283 [M+H]+.

3-Methyl-N-(2-methylquinolin-8-yl)thiophene-2-carboxamide G3

3-Methyl-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinaldine (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product G3. ESI-MS: m/z 283 [M+H]+.

5-Chloro-N-(2-methylquinolin-8-yl)thiophene-2-carboxamide G4

5-Chloro-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinaldine (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product G4. ESI-MS: m/z 303 [M+H]+.

5-Acetyl-N-(2-methylquinolin-8-yl)thiophene-2-carboxamide G5

5-Acetyl-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinaldine (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product G5. ESI-MS: m/z 311 [M+H]+.

3,5-Dibromo-N-(2-methylquinolin-8-yl)thiophene-2-carboxamide G6

3,5-Dibromothiophene-2-carboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinaldine (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product G6. ESI-MS: m/z 427 [M+H]$^+$.

4,5-Dibromo-N-(2-methylquinolin-8-yl)thiophene-2-carboxamide G7

4,5-Dibromothiophene-2-carboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinaldine (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product G7. ESI-MS: m/z 427 [M+H]$^+$.

4-Bromo-N-(2-methylquinolin-8-yl)thiophene-2-carboxamide G8

4-Bromo-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution was added 8-aminoquinaldine (1.0 mmol) and the mixture was stirred for 20 hrs. The mixture was diluted with water and extracted with 2 volumes of ethyl acetate. The organic layers were collected and the solvent was removed by rotary evaporation. The residue is purified by preparative reverse-phase HPLC using a water-acetonitrile gradient to afford the desired product G8. ESI-MS: m/z 348 [M+H]$^+$.

5-Bromo-N-(quinolin-8-yl)thiophene-2-carboxamide H1

5-Bromo-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 6-aminoquinoline (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product H1. ESI-MS: m/z 334 [M+H]$^+$.

N-(quinolin-8-yl)thiophene-2-carboxamide H2

2-Thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinoline (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product H2. ESI-MS: m/z 255 [M+H]$^+$.

5-Methyl-N-(quinolin-8-yl)thiophene-2-carboxamide H3

5-Methyl-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinaldine (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product H3. ESI-MS: m/z 269 [M+H]$^+$.

3-Methyl-N-(quinolin-8-yl)thiophene-2-carboxamide H4

3-Methyl-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinoline (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product H4. ESI-MS: m/z 269 [M+H]$^+$.

5-Chloro-N-(quinolin-8-yl)thiophene-2-carboxamide H5

5-Chloro-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinoline (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product H5. ESI-MS: m/z 289 [M+H]$^+$.

5-Acetyl-N-(quinolin-8-yl)thiophene-2-carboxamide H6

5-Acetyl-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinoline (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product H6. ESI-MS: m/z 297 [M+H]$^+$.

N-(Quinolin-8-yl)benzofuran-2-carboxamide H7

Benzofuran-2-carboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinoline (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product H7. ESI-MS: m/z 289 [M+H]$^+$.

5-Nitro-N-(quinolin-8-yl)thiophene-2-carboxamide H8

5-Nitro-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 6-aminoquinoline (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product H8. ESI-MS: m/z 300 [M+H]$^+$.

4-Bromo-N-(quinolin-8-yl)thiophene-2-carboxamide H9

4-Bromo-2-thiophenecarboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinoline (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product H9. ESI-MS: m/z 334 [M+H]$^+$.

3,5-Dibromo-N-(quinolin-8-yl)thiophene-2-carboxamide H10

3,5-Dibromothiophene-2-carboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinoline (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product H10. ESI-MS: m/z 413 [M+H]+.

4,5-Dibromo-N-(quinolin-8-yl)thiophene-2-carboxamide H11

4,5-Dibromothiophene-2-carboxylic acid (1.0 mmol) and N-(3-dimethylaminopropyl)-N'-ethylcarbodiimide hydrochloride (1.2 mmol) were dissolved in dimethylformamide (5 mL). N,N-Diisopropylethylamine (1.5 mmol) was added and the solution was stirred for 10 min. To this solution 8-aminoquinoline (1.0 mmol) was added, and the mixture was stirred for 20 hrs. The mixture was diluted with water and extracted with 2 volumes of ethyl acetate. The organic layers were collected and the solvent was removed by rotary evaporation. The residue was purified by preparative reverse-phase HPLC using a water-acetonitrile gradient to afford the desired product H11. ESI-MS: m/z 413 [M+H]$^+$.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed:

1. A pharmaceutical composition in a solid form comprising:
   i) a therapeutically effective amount of a compound of the following structural formula:

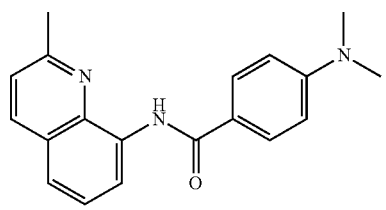 [SMILES: Cc1ccc2cccc(NC(=O)c3ccc(N(C)C)cc3)c2n1]

or a pharmaceutically acceptable salt, solvate, or hydrate thereof; and
   ii) a pharmaceutically acceptable carrier, excipient or diluent.

2. A method for treating one or more symptoms of diabetes in a subject in need thereof comprising administering to the subject an effective amount of the pharmaceutical composition of claim 1.

3. The method of claim 2 wherein the diabetes is type 1.

4. The method of claim 2 wherein the diabetes is type 2.

* * * * *